(12) United States Patent
Kaufmann

(10) Patent No.: US 10,307,189 B2
(45) Date of Patent: Jun. 4, 2019

(54) PROSTHESIS FOR PARTIAL AND TOTAL JOINT REPLACEMENT

(71) Applicant: Robert A. Kaufmann, Pittsburgh, PA (US)

(72) Inventor: Robert A. Kaufmann, Pittsburgh, PA (US)

( * ) Notice: Subject to any disclaimer, the term of this patent is extended or adjusted under 35 U.S.C. 154(b) by 0 days.

(21) Appl. No.: 15/018,846

(22) Filed: Feb. 8, 2016

(65) Prior Publication Data
US 2016/0158018 A1 Jun. 9, 2016
US 2017/0252171 A9 Sep. 7, 2017

Related U.S. Application Data

(62) Division of application No. 14/046,924, filed on Oct. 5, 2013, now Pat. No. 9,289,304.
(Continued)

(51) Int. Cl.
*A61F 2/38* (2006.01)
*A61B 17/72* (2006.01)
(Continued)

(52) U.S. Cl.
CPC ........ *A61B 17/7233* (2013.01); *A61F 2/0811* (2013.01); *A61F 2/30* (2013.01);
(Continued)

(58) Field of Classification Search
CPC .. A61F 2/38; A61F 2/3804; A61F 2002/3813; A61F 2002/3822;
(Continued)

(56) References Cited

U.S. PATENT DOCUMENTS 2,696,817 A 12/1954 Prevo
3,547,115 A 12/1970 Stevens
(Continued)

OTHER PUBLICATIONS

Claus, J. , et al. "The GSB III elbow prosthesis in rheumatoid arthritis: A 2-to 9-year follow up". Acta Orthopaedica (2006); 77:1. pp. 143-148 (Year: 2006).*
(Continued)

*Primary Examiner* — Brian E Pellegrino
*Assistant Examiner* — Rebecca Lynee Zimmerman
(74) *Attorney, Agent, or Firm* — William F. Lang, IV; Lang Patent Law LLC

(57) ABSTRACT

A prosthetic joint is secured to the bones forming the original joint by utilizing strictly mechanical fasteners, for example, a threaded rod engaging a tapped intramedullary canal. Cross locking members may be provided. The need for bone cement is avoided. The prosthetic joint may be used to replace one end of one bone forming the joint, utilizing the naturally occurring end of the other bone. Alternatively, both bone ends may be replaced with prosthetic joint portions. The decision to replace one or both bone ends may be made mid-surgery. The prosthetic joint portions are secured together utilizing ligament reconstruction members made from portions of the patient's tendons or allograft tendons. A bearing forming the interface between the two joint portions is designed to wear in order to protect the remaining components from wear, and to be easily replaced in relatively simple future surgeries.

5 Claims, 16 Drawing Sheets

Related U.S. Application Data

(60) Provisional application No. 61/806,392, filed on Mar. 28, 2013.

(51) Int. Cl.
*A61F 2/08* (2006.01)
*A61F 2/30* (2006.01)

(52) U.S. Cl.
CPC .............. *A61F 2/38* (2013.01); *A61F 2/3804* (2013.01); *A61F 2/08* (2013.01); *A61F 2002/0829* (2013.01); *A61F 2002/0852* (2013.01); *A61F 2002/0888* (2013.01); *A61F 2002/3085* (2013.01); *A61F 2002/30301* (2013.01); *A61F 2002/30433* (2013.01); *A61F 2002/30624* (2013.01); *A61F 2002/3809* (2013.01); *A61F 2002/3813* (2013.01); *A61F 2220/0008* (2013.01)

(58) Field of Classification Search
CPC .. A61F 2002/30329; A61F 2002/30331; A61F 2002/30624; A61F 2002/30688; A61F 2/30749; A61F 2220/0025; A61F 2/0811; A61F 2002/30578; A61F 2/08; A61F 2002/0829; A61F 2002/0888; A61F 2002/30301; A61F 2002/30433; A61F 2002/3085; A61F 2002/3809; A61F 2220/0008; A61B 17/7233
USPC ......... 623/20.23, 20.12, 20.13, 13.14, 13.11, 623/20.14, 23.41
See application file for complete search history.

(56) References Cited

U.S. PATENT DOCUMENTS

| | | | |
|---|---|---|---|
| 3,708,805 A | 1/1973 | Scales et al. | |
| 3,772,709 A | 11/1973 | Swanson | |
| 3,816,854 A * | 6/1974 | Schlein | A61F 2/3804 623/20.12 |
| 3,852,831 A | 12/1974 | Dee | |
| 3,868,730 A | 3/1975 | Kaufer et al. | |
| 3,919,725 A | 11/1975 | Swanson et al. | |
| 3,924,276 A * | 12/1975 | Eaton | A61F 2/4241 623/21.15 |
| 3,939,496 A | 2/1976 | Ling et al. | |
| 3,990,117 A | 11/1976 | Pritchard et al. | |
| 3,991,425 A | 11/1976 | Martin et al. | |
| 4,008,495 A | 2/1977 | Cavendish et al. | |
| 4,057,858 A | 11/1977 | Helfet | |
| 4,079,469 A | 3/1978 | Wadsworth | |
| 4,129,902 A | 12/1978 | Harmon | |
| 4,131,956 A | 1/1979 | Treace | |
| 4,224,695 A | 9/1980 | Grundei et al. | |
| 4,242,758 A | 1/1981 | Amis et al. | |
| 4,280,231 A | 7/1981 | Swanson | |
| 4,293,963 A | 10/1981 | Gold et al. | |
| 4,383,337 A | 5/1983 | Volz et al. | |
| 4,538,306 A | 9/1985 | Doore et al. | |
| 4,681,590 A | 7/1987 | Tansey | |
| 4,712,542 A | 12/1987 | Daniel et al. | |
| 4,840,633 A | 1/1989 | Kallabis et al. | |
| 5,167,666 A | 12/1992 | Mattheek et al. | |
| 5,282,867 A * | 2/1994 | Mikhail | A61F 2/0811 623/13.12 |
| 5,314,484 A | 5/1994 | Huene | |
| 5,376,121 A | 12/1994 | Huene et al. | |
| 5,458,654 A | 10/1995 | Tepic | |
| 5,520,693 A | 5/1996 | McGuire et al. | |
| 5,562,668 A | 10/1996 | Johnson | |
| 5,667,510 A | 9/1997 | Combs | |
| 5,723,015 A | 5/1998 | Risung et al. | |
| 5,782,923 A | 7/1998 | Engelbrecht et al. | |
| 5,879,395 A | 3/1999 | Tornier et al. | |
| 5,989,261 A | 11/1999 | Walker | |
| 6,027,534 A | 2/2000 | Wack et al. | |
| 6,126,691 A | 10/2000 | Kasra et al. | |
| 6,162,253 A | 12/2000 | Conzemius et al. | |
| 6,290,725 B1 | 9/2001 | Weiss et al. | |
| 6,306,171 B1 | 10/2001 | Conzemius | |
| 6,325,804 B1 | 12/2001 | Wenstrom, Jr. et al. | |
| 6,379,387 B1 * | 4/2002 | Tornier | A61F 2/3804 623/20.12 |
| 6,475,242 B1 | 11/2002 | Bramlet | |
| 6,514,288 B2 | 2/2003 | Meulink et al. | |
| 6,517,541 B1 | 2/2003 | Sesic | |
| 6,699,290 B1 | 3/2004 | Wack et al. | |
| 6,716,248 B2 | 4/2004 | Huene | |
| 6,767,368 B2 | 7/2004 | Tornier | |
| 6,878,150 B1 | 4/2005 | McGuire et al. | |
| 6,890,357 B2 | 5/2005 | Tornier | |
| 6,905,513 B1 * | 6/2005 | Metzger | A61F 2/08 623/20.14 |
| 6,949,102 B2 | 9/2005 | Andrews | |
| 6,997,957 B2 | 2/2006 | Huene | |
| 7,247,170 B2 | 7/2007 | Graham et al. | |
| 7,850,737 B2 | 12/2010 | Morrey | |
| 2003/0208276 A1 * | 11/2003 | Berelsman | A61F 2/3804 623/20.11 |
| 2005/0049710 A1 | 3/2005 | O'Driscoll et al. | |
| 2006/0052878 A1 | 3/2006 | Schmieding | |
| 2007/0185584 A1 | 8/2007 | Kaufmann et al. | |
| 2009/0125114 A1 * | 5/2009 | May | A61B 17/1764 623/20.14 |
| 2009/0228017 A1 | 9/2009 | Collins | |
| 2010/0179661 A1 | 7/2010 | Berelsman et al. | |
| 2010/0241239 A1 | 9/2010 | Smith | |
| 2011/0040339 A1 * | 2/2011 | Solomon | A61B 17/8605 606/312 |
| 2012/0109322 A1 | 5/2012 | Gonzalez-Hernandez | |
| 2013/0226306 A1 * | 8/2013 | Naidu | A61F 2/4241 623/21.12 |
| 2014/0277550 A1 | 9/2014 | Lindsay et al. | |

OTHER PUBLICATIONS

Adolfsson L, Nestorson J. The Kudo Humeral Component as Primary Hemiarthroplasty in Distal Humeral Fractures, J Shoulder Elbow Surg 2012;21 (4):451-455.

A. J. Donaldson, H. E. Thomson, N. J. Harper and N. W. Kenny. Bone cement implantation syndrome, BR J Anaesth 2009; 102: 12-22.

Bennett JB, Mehihoff TL. Total Elbow Arthroplasty: Surgical Technique, J Hand Surg AM 2009;34 (5):933-939.

K. J. Burkhart, G. Stein, E. Skooras, and L. P. Muller, Revisionsendoprothetik des Ellenbogens, Der Unfallchirurg (2010) 996-1005.

Burkhart KJ, Nijs S, Mattyasovszky SG et al. Distal Humerus Hemiarthroplasty of the Elbow for Comminuted Distal Humeral Fractures in the Elderly Patient, J Trauma 2011;71 (3):.

Cross MB, Sherman SL, Kepler CK et al. The Evolution of Elbow Arthroplasty: Innovative Solutions to Complex Clinical Problems, J Bone Joint Surg AM 2011;92 Suppl 2:98-104.

Dee R. Total Replacement Arthroplasty of the Elbow for Rheumatoid Arthritis, J Bone Joint Surg BR 1972;54 (1):88-95.

Duncan CP, Masril BA. Fractures of the Femur After Hip Replacement, Instr Course Lect 1995;44:293-304.

Kim JM, Mudgal CS, Konopka JF et al. Complications of Total Elbow Arthroplasty, J AM Acad Orthop Surg 2011;19 (6):328-339.

Lucie Krenek, Eugene Farng, David Zigmond, and Nelson F. SooHoo, Complication and Revision Rates Following Total Elbow Arthroplasty, JHS, (2011) 36A: 68-73.

Matthew P. Abdel and Bernard F. Morrey, Implications of Revision Total Elbow Arthroplasty on Blood Transfusion, J Shoulder Elbow Surg (2010) 19:190-195.

O'Driscoll SW, Morrey BF. Periprosthetic Fractures about the Elbow, Orthop Clin North AM 1999;30 (2):319-325.

Scott F. M. Duncan, John W. Sperling, and Bernard Morrey, Incidence and Risk Factors for Blood Transfusion in Total Elbow Arthroplasty, J Shoulder Elbow Surg (2008) 961-962.

(56) References Cited

OTHER PUBLICATIONS

Tyson K. Cobb and Bernard F. Morrey, Total Elbow Anthroplasty as Primary Treatment for Distal Humerus Fractures in Elderly Patients, J Bone Joint Surg (1997) 826-832.
Zinon T. Kokkalis, Christopher C. Schmidt, and Dean G. Sotereanos, Elbow Arthritis: Current Concepts, JHS (2009) 34A: 761-768.
Acclaim Total Elbow System, DePuy Orthopaedics, Inc., 2004.
Latitude Total Elbow Prosthesis, Tornier, Inc. 2011.
The Sorbie-Questor Total Elbow System Surgical Technique, Wright Medical Technology Inc., 1997.
Total Elbow System Surgical Procedure, Solar Upper Extremity System, Howmedica Osteonics, 2000.
Garrett JC, Ewald FC, Thomas WH et al. Loosening Associated with G.S.B. Hinge Total Elbow Replacement in Patients with Rheumatoid Arthritis, Clin Orthop Relat Res 1977; (127):.
Gschwend N, Simmen BR, Matejovsky Z. Late Complications in Elbow Arthroplasty, J Shoulder Elbow Surg 1996;5 (2 Pt 1):86-96.
G. Stein, O. Weber, K. J. Burkhart, and L. P. Muller, Ellenbogengelenk-Totalendoprothese, DER Unfallchirurg (2010) 1006-1012.
Hildebrand KA, Patterson SD, Regan WD et al. Functional Outcome of Semiconstrained Total Elbow Arthroplasty, J Bone Joint Surg AM 2000;82-A (10):1379-1386.
Hurri L, Pulkki T, Vainio K, Arthroplasty of the Elbow in Rheumatoid Arthritis, ACTA Chir Scand 964;127:459-465.
Kai-Nan An, Kinematics and Constraint of Total Elbow Anthroplasty, J Shoulder Elbow Surg (2005) 14(15): 168S-173S.

Ken Yamaguchi, Robert A. Adams, and Bernard F. Morrey, Infection After Total Elbow Anthroplasty, J Bone Joint Surg, (1998) 80A (4) 481-491.
Zimmer Conrad/Morrey Total Elbow, Zimmer, Inc., 2009.
J. M. Brinkman et al., Failure Mechanisms in Uncemented Kudo Type 5 Elbow Prosthesis in Patients With Rheumatoid Arthritis, Ada Orthopaedica (2007) 78(2), 263-270.
C. Spormann et al., Treatment Strategies for Periprosthetic Infections After Primary Elbow Anthroplasty, Journal of Shoulder and Elbow Surgery (2012) 21, 992-1000.
J. Sanchez Dotelo et al., Periprosthetic Humeral Fractures After Total Elbow Anthroplasty, Journal of Bone and Joint Surgery (2002), 1642-1650.
F. Akpinar et al., A Morphometric Study of the Humerus for Intramedullary Fixation, Tobuko J. Exp. Med. (2003) 199, 35-42.
I. H. Jeon et al., Incidence and Implications of Early Postoperative Wound Complications After Total Elbow Anthroplasty, J. Shoulder and Elbow Surgery (2011), 20, 857-865.
P. S. Ray et al., Total Elbow Anthroplasty as Primary Treatment for Distal Humeral Fractures in Elderly Patients, Injury Int. J. Care Injured 31 (2000) 687-692.
D. Tokunaga et al., Periprosthetic Ulnar Fracture After Loosening of Total Elbow Anthroplasty Treated by Two Stage Implant Revision, J. Shoulder Elbow Surg. Nov./Dec. 2006, 23-6.
Latitude Total Elbow Surgical Technique, Tornier, Inc.
Discovery Elbow System, Biomet Orthopedics, Inc.

* cited by examiner

PROSTHESIS FOR PARTIAL AND TOTAL JOINT REPLACEMENT

CROSS REFERENCE TO RELATED APPLICATION

This application is a divisional of U.S. patent application Ser. No. 14/046,924, which was filed on Oct. 5, 2013, and entitled "Prosthesis for Partial and Total Joint Replacement.

TECHNICAL FIELD

The present invention relates to prosthetic joints. More specifically, a prosthetic joint having an improved connection to the medullary canals is provided. Additionally, a prosthetic joint that may be used for either partial or total joint replacement is provided.

BACKGROUND INFORMATION

There are three bones in the elbow: the humerus, the ulna, and the radius. These three bones articulate in the ulnohumeral, radiohumeral and radioulnar joints. Each of the joint surfaces is covered with articular cartilage and motion occurs at these articulations with distinct motion profiles. The cartilage allows the bones to slide easily against one another as the joint moves through its range of motion. The ulnohumeral joint is most essential for transmitting forces through the elbow.

Degenerative joint diseases such as Osteoarthritis as well as inflammatory arthritides such as Rheumatoid arthritis commonly affect the elbow joints and causes articular degeneration and marginal bone formation. In post-traumatic settings, where surgical efforts have failed to restore adequate alignment, post-traumatic arthritis may set in and become symptomatic with patients experiencing pain and a loss of range of motion. Whether idiopathic, inflammatory or post-traumatic, elbow arthritis is often painful and may interfere with function of the entire arm.

Initial non-operative intervention often includes splinting and steroid injections. Elbow joint synovectomy and debridement of arthritic spurs are surgical options when the cartilage damage is limited. Arthodesis (i.e., joint fusion) is an option for very damaged joints and is rarely used as elbow range of motion is sacrificed. Functional requirements of the patient often necessitate a durable solution that maintains range of motion. Accordingly, numerous prior efforts have been undertaken to replace this joint.

Whereas degenerative joint diseases usually affect patients after the fifth decade of life, traumatic conditions may cause elbow joint impairment in younger age groups. Elbow fractures such as of the distal humerus or olecranon often exhibit intra-articular involvement, which can lead to permanent cartilage damage despite the best surgical reconstruction efforts. This is particularly true when anatomic reconstruction of the joint surfaces is not successful or if osteochondral portions are missing as may occur in open injuries. In these settings, consideration for a primary joint replacement as an option may be given. Often, only a portion of the elbow joint is injured such as the distal humerus and it may benefit from reconstruction. High energy injuries such as Motorcycle accidents may damage the distal humerus of younger patients and leave the ulna and radius relatively uninjured. Thus, the ability to replace either the distal humerus only (hemiarthroplasty) or the entire elbow (total arthroplasty) is quite helpful.

Initial joint replacement efforts were done as early as 1947, when surgeons employed custom made hinges to replace elbow joints. However, the results of these early efforts were characterized by implant loosening, instability and poor clinical results. Hurri L, Pulkki T, Vainio K. *Arthroplasty of the Elbow in Rheumatoid Arthritis*, ACTA CHIR SCAND 964; 127:459-465; Dee R. *Total Replacement Arthroplasty of the Elbow for Rheumatoid Arthritis*, J BONE JOINT SURG BR 1972; 54 (1):88-95; Cross M B, Sherman S L, Kepler C K et al. *The Evolution of Elbow Arthroplasty: Innovative Solutions to Complex Clinical Problems*, J BONE JOINT SURG AM 2011; 92 Suppl 2:98-104. In the 1970s, the first simple hinged elbow prostheses were implanted using cementing techniques. Cross M B, Sherman S L, Kepler C K et al. *The Evolution of Elbow Arthroplasty: Innovative Solutions to Complex Clinical Problems*, J BONE JOINT SURG AM 2011; 92 Suppl 2:98-104. This improved the stability of the construct, but still resulted in rates of loosening of up to 50%. Garrett J C, Ewald F C, Thomas W H et al. *Loosening Associated with G. S. B. Hinge Total Elbow Replacement in Patients with Rheumatoid Arthritis*, CLIN ORTHOP RELAT RES 1977; (127):170-174. As a result of these observations, different design concepts have emerged: linked, unlinked, convertible and modular elbow prostheses.

Linked, or "semi-constrained," prostheses are commonly used implants and employ a "sloppy hinge" mechanism that allows for some varus, valgus, and rotational movement. The linked design offers superior stability and dislocations of these joints are rare, however, the constrained design transfers forces through the bone-cement or bone-implant interface which then results in significant loosening rates.

Unlinked or "unconstrained" prosthesis designs work without a mechanical linkage between the components. These prostheses can be implanted while maintaining good bone stock and offer decreased polyethylene wear when compared to their linked counterparts. Since there is no mechanical linkage between the components, the stability of the construct relies greatly on the soft tissues around the elbow. It is believed that a well-balanced soft tissue envelope reduces stress at the bone-cement and bone-implant interfaces which results in lower loosening rates compared to linked designs. Understandably, this reliance on soft tissues to maintain stability results in higher rates of instability and joint dislocation compared to linked designs. These characteristics prevent the use of an unlinked prosthesis in situations where soft tissue integrity is poor or extensive bone loss has occurred.

Total elbow arthroplasty systems have been developed that allow intra-operative decision making with regards to what type of implant may be best suited. "Convertible" systems have been developed that allow the placement of either a semi-constrained or an unconstrained construct based on the soft tissue integrity of the patient. These designs allow intraoperative conversion between unlinked and linked inplants as dictated by the integrity of the soft tissues and bone.

Modular arthroplasty relates to replacement of a portion of the elbow joint. Total elbow arthroplasty may not be an ideal solution for younger patients. This group may benefit from replacement of only those regions that are damaged while preserving unaffected joint surfaces. On occasion, the distal humerus is severely injured with relative sparing of the proximal ulna or radius. In some instances, such as high energy motor vehicle accidents, the distal humerus is not salvageable. Thus, the ability to replace either the distal humerus only (hemiarthroplasty) or the entire elbow (total arthroplasty) is quite helpful. A modular system would then also allow the surgeon to add implants at a later time as subsequent wear and tear of the remaining native joint surfaces may occur.

A currently available modular elbow arthroplasty system is the UNI-Elbow Radio Capitellum System (Small Bone Innovations) that allows for replacement of the radio-humeral joint in isolation. It is a Uni-compartmental arthroplasty of the elbow where the lateral side of the elbow is replaced in isolation. Additionally, the Latitude Total Elbow prosthesis (Tornier, USA) is a total elbow replacement system whose distal humerus component matches native anatomy closely and can be used in isolation (hemiarthroplasty) in instances where the ulna is in good condition.

In a case series on hemiarthroplasty for distal humerus fractures in elderly patients using the Latitude System mainly good to excellent short-term results based on a Mayo score and good functional results were achieved. None of the complications required implant removal and only in one case did progressive osteoarthritis of the proximal ulna and radius occur. These results only represented a mean follow-up of 12.1 months, however, and therefore must be interpreted cautiously. Burkhart K J, Nijs S, Mattyasovszky S G et al. *Distal Humerus Hemiarthroplasty of the Elbow for Comminuted Distal Humeral Fractures in the Elderly Patient*, J TRAUMA 2011; 71 (3):635-642. The use of the Kudo prosthesis for hemiarthroplasty purposes has been described in a small case series with reasonable functional outcome after a mean of 4 years status after implantation. However, radiographic signs of attrition indicate that this implant may not be ideally suited for this role. Adolfsson L, Nestorson J. *The Kudo Humeral Component as Primary Hemiarthroplasty in Distal Humeral Fractures*, J SHOULDER ELBOW SURG 2012; 21 (4):451-455.

At this time, all commercially available implants whether linked, unlinked, convertible or modular are cemented in place. Even though this offers a quick, reliable, and relatively durable bone-to-implant fixation, there are significant limitations. The most noteworthy is that the implant and cement mantle is difficult to remove if this is required such as in the face of an infection or peri-prosthetic fracture. If the implant is merely loose and improved fixation is required, then the cement can be removed where it is loose and left in place where it is often quite inaccessible. It is when eradicating an infection, however, when the entire cement mantle needs to be accounted for and eliminated, that the surgical effort to accomplish this becomes quite involved. Damage to the soft tissues as well as neurovascular structures can occur and, even in the best of circumstances, significant bone stock is removed along with the cement. To address the subsequent bone loss, Zimmer (Warsaw, Ind., USA) markets a method whereby new bone is introduced through impaction grafting around a repeat cement mantle when a second implant is placed in a revision arthroplasty setting. With patients living longer and more active lives, it is of paramount importance to offer an implant that can be rigidly placed but then also removed without undue trauma to the bones and the soft tissue envelope into which they gain fixation.

The use of cement has the potential added drawback of causing thermal osteonecrosis. The cement is inserted at room temperature into the intramedullary canal to secure an implant and employs an exothermic reaction to become hard. This high temperature may damage the surrounding bone and potentially compromise its ability to heal after implant installation. It may also hinder new bone growth advantageous to helping secure the implant after installation.

Elbow arthroplasty carries serious potential complications. The most dire complication is the development acute, subacute, or chronic infections. The soft tissue envelope that surrounds the elbow is thin, thereby making this location vulnerable to this complication. The incidence of deep infections after Total Elbow Arthroplasty lies between 3 and 8%. Kim J M, Mudgal C S, Konopka J F et al. *Complications of Total Elbow Arthroplasty*, J AM ACAD ORTHOP SURG 2011; 19 (6):328-339; Tachihara A, Nakamura H, Yoshioka T et al., *Postoperative Results and Complications of Total Elbow Arthroplasty in Patients with Rheumatoid Arthritis: Three Types of Nonconstrained Arthroplasty*, MOD RHEUMATOL 2008; 18 (5):465-471; Gschwend N, Simmen B R, Matejovsky Z. *Late Complications in Elbow Arthroplasty*, J SHOULDER ELBOW SURG 1996; 5 (2 Pt 1):86-96. The causative organism is usually *Staph. Aureus* or *Epidermidis. Staph. Epidermidis* is considered more virulent due to its ability to form biofilms. In most patients the time span between index arthroplasty and revision is more than three weeks and spontaneous drainage after ten days may be indicative of deep bacterial colonization. Kim J M, Mudgal C S, Konopka J F et al. *Complications of Total Elbow Arthroplasty*, J AM ACAD ORTHOP SURG 2011; 19 (6):328-339.

Infections after Total Elbow Arthroplasty should be managed aggressively and resection arthroplasty may be warranted. Resistant infections are managed by hardware removal and debridement of all affected structures including bone, soft tissues and bone cement. Because of the significant recurrence rate, re-implantation should only be performed cautiously given that prosthesis survival is significantly diminished in those cases (77% 3-year, 48% 8-year survival). Kim J M, Mudgal C S, Konopka J F et al. *Complications of Total Elbow Arthroplasty*, J AM ACAD ORTHOP SURG 2011; 19 (6):328-339. Given that the cement must be removed in addition to the implant in order to eradicate the infection, the likelihood of having reasonable bone stock remaining after the implant and bone cement has been removed is low. Realizing the low survival rate of the second implant, the decision to re-implant a new arthroplasty is often met with significant resistance. Most patients do not want to undergo a re-implantation effort. Having an implant system that contains no cement and can be removed much more easily when compared to its cemented brethren would minimize the bone loss associated with implant removal and increase the likelihood of subsequent re-implantation.

Peri-prosthetic loosening may occur after implantation and often requires revision surgical efforts. Bennett J B, Mehlhoff T L. *Total Elbow Arthroplasty: Surgical Technique*, J HAND SURG AM 2009; 34 (5):933-939. To ensure longevity, patients must be willing to accept a lifelong 5-lb lifting restriction to that extremity. Bennett J B, Mehlhoff T L. *Total Elbow Arthroplasty: Surgical Technique*, J HAND SURG AM 2009; 34 (5):933-939. In general, the ulnar components are at the highest risk for aseptic loosening and this risk is associated with the quality of fixation. An estimated 7 to 17% of all total elbow arthroplasties show clinical loosening, whereas the rate of radiographic loosening is even higher. Kim J M, Mudgal C S, Konopka J F et al. *Complications of Total Elbow Arthroplasty*, J AM ACAD ORTHOP SURG 2011; 19 (6):328-339. Tachihara A, Nakamura H, Yoshioka T et al. *Postoperative Results and Complications of Total Elbow Arthroplasty in Patients with Rheumatoid Arthritis: Three Types of Nonconstrained Arthroplasty*, MOD RHEUMATOL 2008; 18 (5):465-471; Gschwend N, Simmen B R, Matejovsky Z. Late *Complications in Elbow Arthroplasty*, J SHOULDER ELBOW SURG 1996; 5 (2 Pt 1):86-96.

The design of a semi-constrained elbow prosthesis, allowing for an element of varus-valgus laxity, is thought to reduce the incidence of aseptic loosening. Ensuring both accurate implant positioning as well as excellent cement fixation are crucial to minimize stress on the implant as well as the development of aseptic loosening. Kim J M, Mudgal C S, Konopka J F et al. *Complications of Total Elbow Arthroplasty*, J AM ACAD ORTHOP SURG 2011; 19 (6):328-339. Revision arthroplasty should be considered in the setting of instability and pain. When this happens, both the prosthesis and cement should be removed using adequate instruments. Sometimes an osteotomy or the creation of bone windows is needed. Cementless implantation is rarely employed. Uncemented elbow arthroplasty in rheumatoid arthritis patients was described utilizing the Kudo prosthesis which demonstrated a high rate of aseptic loosening (7 of 49) within the ulnar component ultimately leading to an inability to recommend this implant without the use of cement fixation. Brinkman J M, de Vos M J, Eygendaal D. *Failure Mechanisms in Uncemented Kudo Type 5 Elbow Prosthesis in Patients with Rheumatoid Arthritis: 7 of 49 Ulnar Components Revised Because of Loosening After 2-10 years*, ACTA ORTHOP 2007; 78 (2):263-270.

Periprosthetic fracture after primary total elbow arthroplasty occurs with an incidence of 5 to 29% with underlying causes including direct trauma, osteoarthritis, or aseptic loosening. Kim J M, Mudgal C S, Konopka J F et al. *Complications of Total Elbow Arthroplasty*, J AM ACAD ORTHOP SURG 2011; 19 (6):328-339. Tachihara A, Nakamura H, Yoshioka T et al. *Postoperative Results and Complications of Total Elbow Arthroplasty in Patients with Rheumatoid Arthritis: Three Types of Nonconstrained Arthroplasty*, MOD RHEUMATOL 2008; 18 (5):465-471; Hildebrand K A, Patterson S D, Regan W D et al. *Functional Outcome of Semiconstrained Total Elbow Arthroplasty*, J BONE JOINT SURG AM 2000; 82-A (10):1379-1386; O'Driscoll S W, Morrey B F. *Periprosthetic Fractures about the Elbow*, ORTHOP CLIN NORTH AM 1999; 30 (2):319-325. Periprosthetic elbow fracture treatment has been characterized in the literature. O'Driscoll S W, Morrey B F. *Periprosthetic Fractures about the Elbow*, ORTHOP CLIN NORTH AM 1999; 30 (2):319-325; Foruria A M, Sanchez-Sotelo J, Oh L S et al. *The Surgical Treatment of Periprosthetic Elbow Fractures Around the Ulnar Stem Following Semiconstrained Total Elbow Arthroplasty*, J BONE JOINT SURG AM 2011; 93 (15): 1399-1407; Sanchez-Sotelo J, O'Driscoll S, Morrey B F. *Periprosthetic Humeral Fractures After Total Elbow Arthroplasty: Treatment with Implant Revision and Strut Allograft Augmentation*, J BONE JOINT SURG AM 2002; 84-A (9):1642-1650.

Not all fractures require surgical treatment and immobilization may be sufficient in some cases. With significant displacement, open reduction and internal fixation should be performed. In these cases the bone stock at the fracture site dictates the technique used such as cerclage wiring or plate fixation. A significant hardship when treating periprosthetic fractures involves the cement mantle that surrounds the implant. As it lies within the fractured bone and exhibits no healing capability, the cement often has to be removed and then the void filled with bone graft. Not all periprostetic fractures are associated with implant loosening yet frequently these two occur in combination mandating a revision-arthroplasty effort in addition to the fracture open reduction and internal fixation. Sanchez-Sotelo J, O'Driscoll S, Morrey B F. *Periprosthetic Humeral Fractures After Total Elbow Arthroplasty: Treatment with Implant Revision and Strut Allograft Augmentation*, J BONE JOINT SURG AM 2002; 84-A (9):1642-1650. Some cases even require two-staged treatment where fracture union is achieved first and revision arthroplasty is done in a second step. Tokunaga D, Hojo T, Ohashi S et al. *Periprosthetic Ulnar Fracture After Loosening of Total Elbow Arthroplasty Treated by Two-Stage Implant Revision: A Case Report*, J SHOULDER ELBOW SURG 2006; 15 (6):e23-26. If significant loss of bone stock is present within the distal humerus or proximal ulna, successful surgical revision may not be possible leading to salvage options such as an arthrodesis or leaving the elbow flail or even consideration of an amputation.

Other complications may occur that are unrelated to the method of component fixation. For example, ulnar nerve irritation is a concern with any extensive surgery around the elbow and triceps insufficiency may occur either in the acute or later stages.

Bone cement implantation syndrome (BCIS) is a unique problem associated with cement fixation of an implant. It occurs primarily in association with cemented Total Hip arthroplasty. It is characterized by hypoxia, hypotension or both and/or unexpected loss of consciousness occurring around the time of cementation, prosthesis insertion, reduction of the joint or, occasionally, limb tourniquet deflation in a patient undergoing cemented bone surgery. Bone cement implantation syndrome (BCIS) is poorly understood and yet is an important cause of intraoperative mortality and morbidity in patients undergoing cemented hip arthroplasty and may also be seen in the postoperative period in a milder form causing hypoxia and confusion. Currently, when preparing for cementation, the anesthesiologist is informed that the cementation process is being started so as to closely monitor any adverse intra-operative effect. Our design does not include cement fixation at all and, thereby, eliminates this risk. A. J. Donaldson, H. E. Thomson, N. J. Harper and N. W. Kenny. *Bone cement implantation syndrome*, BR J ANAESTH 2009; 102: 12-22.

Different devices for the prosthetic treatment of the elbow joint have been developed. Commercially available systems for elbow arthroplasty at the present time include:
1. Solar® total elbow system, sold by Stryker Orthopaedics, which is a linked hinge design that employs cement fixation.
2. GBS III Elbow System, sold by Sulzer Orthopedics, which is an unlinked, cemented total elbow system.
3. Coonrad/Morrey Total Elbow, sold by Zimmer Inc., which is a linked hinge system that employs cement fixation.
4. Discovery elbow system, sold by Biomet, which is a linked, cemented total elbow system.
5. IBP Elbow System, sold by Biomet, which is a linked, cemented total elbow system.
6. Biomet Huene BiAxial Elbow System, sold by Biomet, which is a linked, cemented total elbow system.
7. DePuy Pritchard ERS (DePuy, USA)—not currently marketed
8. Latitude Total Elbow, which is a modular, convertible, cemented total elbow system.
9. Stryker Howmedica Souter-Strathclyde, which is sold by Stryker, and which is not currently marketed.
10. Stryker Howmedica Kudo type 5 elbow prosthesis, sold by Stryker, and which is not currently marketed.
11. Stryker Osteonics elbow prosthesis, sold by Styker, which is a linked, cemented total elbow system. This system is not currently marketed.
12. Volz AHSC elbow prosthesis, which is not presently marketed.

13. Wright Sorbie-Questor Total Elbow Systems, sold by Wright, which is an unlinked, cemented total elbow system. This system is not currently marketed.
14. Acclaim Total Elbow System, sold by DePuy, which is a convertible, cemented total elbow system. This system is not currently marketed.
15. Biopro Total Elbow System, which is sold by Biopro Inc., USA. This system is not currently marketed.

All of the above elbow prostheses are secured to the respective bones with bone cement and, therefore, carry all of the disadvantages inherent in bone cement.

Numerous other elbow prostheses have been proposed. For example, U.S. Pat. No. 2,696,817 discloses a prosthetic elbow joint comprising two threaded shafts that are separately inserted into the medullary canals. The threads of each shaft cut mating threads or grooves in the walls of the bone cavity to prevent axial displacement and rotational displacement. After installation into the respective bones, these shafts are connected with a low friction bearing.

U.S. Pat. No. 3,547,115 discloses a prosthetic replacement of the articular surface of the distal humerus that is attached by trimming the bone to match the inner surface of the prosthesis and is locked in place by a keyhole-type mechanism. An intramedullary stem fixation method is not intended. This patent only replaces the distal humerus.

U.S. Pat. No. 3,708,805 discloses a prosthetic elbow joint. The humeral member and ulnar member are connected to form a hinge. The male portion of the hinge corresponds to the surface of the female portion of the hinge to avoid tissue being trapped therein. The stems used to cement each component to the bone are non-round to prevent rotation, and tapered to facilitate removal. The ulnar stem is curved eight inches, and the humerus stem is curved three inches. The elbow joint itself is angled to correspond to a natural elbow. This joint is designed for assembly prior to insertion. The hinge appears to prohibit any varus and valgus laxity.

U.S. Pat. No. 3,772,709 discloses an elbow prosthesis having a humeral component made of steel, and an ulnar component made of silicone. The components are held together using a metal pin, and are secured to the respective bones using cement.

U.S. Pat. No. 3,816,854 discloses a prosthesis for total arthroplasty of the elbow joint. The humeral and ulnar components are cemented to the bones with stems having a square cross-section. The ulnar component includes a cylindrical polyethylene bearing that articulates with a mating concave cylindrical surface defined by the humeral component.

U.S. Pat. No. 3,852,831 discloses an endoprosthetic elbow joint. The elbow joint includes a humeral component including a cylindrical bearing surface that is widest at its ends, tapering to a narrow center. This component articulates with an ulnar component that is saddle shaped. The wear surface of the ulnar component can be releasably connected with a dovetail connection. The humeral and ulnar components are retained together by the patient's joint capsule, making this an unconstrained joint.

U.S. Pat. No. 3,868,730 discloses a knee or elbow prosthesis. This prosthesis incorporates a coupled ball and socket connection. Although the title indicates that either an elbow or knee could be replaced, this reference is directed primarily towards knee replacement. A ball on a connecting rod extending upwardly from the tibial component is enclosed by a high density polyethylene socket insert retained within the bottom of the femoral component. The joint is designed to permit a slight degree of twisting or wobbling.

U.S. Pat. No. 3,919,725 discloses a hingeless endoprosthetic device for the elbow joint that comprises humeral and ulnar components. The cylindrical humeral surface is intramedullary fixed. The complementary ulnar component is made from silicone and sits within the ulna. The absence of long stems going into the bone is described as an advantage by this reference, providing for ease of installation and less removal of bone. The hingeless design is called advantageous due to the ease of installation and reduced chances of loosening. This unconstrained device requires that the patient's natural soft tissues are functional.

U.S. Pat. No. 3,939,496 discloses an endoprosthetic joint. The joint includes a humeral component having a pair of spherical bearing members. The ulnar component has a bearing block. Each component is secured on the bone by a long, grooved stem that is anchored by acrylic cement. The grooves key the stem to the acrylic. When installed, a pin passes through the bearings and bearing block to form a hinge. Once the joint capsule heals, the pin is removed to reduce distraction stresses. This joint is, therefore, convertible between a constrained and unconstrained design.

U.S. Pat. No. 3,990,117 discloses an implantable elbow prosthetic joint with cemented stems that articulate in a simple hinged mechanism. Varus and valgus forces are accounted for by allowing "wobble" to avoid damaging the pin assembly, and to place these forces between the shoulders of the implant.

U.S. Pat. No. 3,991,425 discloses a prosthetic joint. The prosthetic joint includes ceramic components having mating concave and convex condylar surfaces. Intersecting lands are provided for stopping motion at the joint's extended and contracted positions. Each of the mating components also includes a stem for implantation in the appropriate medullary canals.

U.S. Pat. No. 4,008,495 discloses a prosthetic bone joint. This joint is designed for minimal bone removal. The humeral component is a pair of frustoconical shapes joined at their narrow ends, which is installed by wedging the component into the intracondylar notch. The ulnar component is made from polymer, and includes a convex bearing surface. The ulnar component is held in place by a bone screw as well as acrylic cement.

U.S. Pat. No. 4,057,858 discloses an elbow prosthesis. This prosthesis includes a humeral component defining a groove in the shape of the helix for mating with a concave surface of the ulnar component. The obliquity of the groove within the trochlea allows the ulnar implant to move into valgus during elbow extension and varus in flexion. A second groove may mate with a radial component. This prosthesis is therefore unconstrained. All components include stems that are secured to the bone by cement.

U.S. Pat. No. 4,079,469 discloses an elbow joint endoprosthesis. The humeral component defines a T-shaped channel for receiving an I shaped portion of the ulnar component. The humeral component includes short longitudinal and transverse keys for securing to the bone. The humeral component also includes a surface for bearing against a radial component. The humeral component is made from polymer, and the ulnar component is made from chrome cobalt. The joint allows minimal varus and valgus yet allows for flexion and extension motion.

U.S. Pat. No. 4,129,902 discloses an elbow prosthesis. The humeral component is connected to an ulnar component by a shaft on the humeral implant and a sleeve on the ulnar implant, providing for hinged articulation between these components. Both implants include tapered stems that are cemented into the bone. A radial implant includes a metal shaft that rotates within a polymer sleeve, and is connected to the humeral component by a chain.

U.S. Pat. No. 4,131,956 discloses an elbow prosthesis. The humeral component includes a U-shaped section holding a non-rotatable polyethylene head. The ulnar component includes a corresponding curved surface for forming an unconstrained joint. Both components include spikes that are cemented into the bone.

U.S. Pat. No. 4,224,695 discloses an endoprosthetic elbow joint. The joint provides a hinged connection between the humeral component, ulnar component, and radial component. The radial component permits rotation around the axis of the radius as well as around the hinge joint. No varus and valgus laxity is allowed between the humerus and ulna.

U.S. Pat. No. 4,242,758 discloses an elbow prosthesis. The humeral components are a tube shaped metal piece with three generally spherical surfaces. A very accurate reproduction of the distal humerus articular surface is provided. It can be used either with an ulnar or a radial replacement or in isolation in which it acts as a hemi-arthroplasty. The ulnar component includes a concave plastic bearing surface with a metal support. The radial component includes a metal pin with a plastic, concave bearing surface. The joint appears unconstrained.

U.S. Pat. No. 4,280,231 discloses an elbow prosthesis. The humeral component includes a pair of sides connected by a cylindrical cross member. The ulnar component has a hook for engaging the cylindrical cross member. Both components include stems for securing to the bones with acrylic cement. The humeral member also includes a surface for engaging the radius.

U.S. Pat. No. 4,293,963 discloses an unconstrained elbow prosthesis. The prosthesis includes a humeral component having an elongated stem and a substantially cylindrical, convex articulating surface. The ulnar component includes a metal retainer with a polyethylene bearing. The metal retainer includes an elongated stem depending from a metal base, and which is slightly curved. The bearing includes a concave cylindrical cavity for receiving the cylinder of the humeral component. A limited amount of medial-lateral motion in addition to flexion and extension is allowed.

U.S. Pat. No. 4,383,337 discloses an elbow prosthesis. The humeral member has a stem and a flange on either side for retaining a bushing as well as a spherical surface for engaging a radial member or a radius. The ulnar member has a stem, a concave surface, and a central projection ending in a cylinder. The projection fits within the bearing. The radial member includes a concave surface. This implant is intended to be a semi constrained joint. The patent claims that the joint is capable of handling up to 50 kg of force.

U.S. Pat. No. 4,538,306 discloses an elbow prosthesis having a humeral component consisting of a sleeve with a circumferential slot. A cylindrical sliding member fits inside the sleeve, abutted by the sides of a slot cut into the humerus. The shaft is inserted through the slot in the sleeve, and secured to the sliding member. The shaft is secured within a hole in the ulna. The shaft and sliding member can, therefore, pivot with respect to the sleeve, forming a hinge. The shaft includes ridges for better retention within the ulna.

U.S. Pat. No. 4,681,590 discloses a femoral stem prosthesis. The prosthesis includes an elongated stem portion, and a ball shaped head. The stem portion includes one or more elongated resilient spring strips which are acted upon by an adjustable screw to cause the spring strips to bow outwardly into engagement with the canal walls.

U.S. Pat. No. 4,840,633 discloses a cementless endoprosthesis. The prosthesis includes a stem that is tapered towards its distal end. A pair of windows are defined the proximal area of the stem. The endoprosthesis further includes a screw spindle having a broad flanged thread in the form of a helix. The thread projects from the windows on either side of the endoprosthesis. Turning the screw spindle causes the helical broad flanged thread to cut into the adjacent bone structure, thereby securing the implant in place. This endoprosthetic stem provides for a load transmission exclusively into the proximal portion of the bone, while the distal portion is free of axial loads.

U.S. Pat. No. 5,167,666 discloses an endoprosthesis for a femur. The endoprosthesis includes a stem that is hollow, slotted, flexible and intended to avoid placing pressure on the bone at this point. A collar and clamping cone are located at the upper end of the endoprosthesis. A tension anchor includes a screw that passes through the femur and is fastened to the prosthesis collar.

U.S. Pat. No. 5,314,484 discloses a biaxial elbow joint replacement. The joint replacement includes a hinge block having an ulnar pivot as well is a humerus pivot. Each pivot permits movement through about 90°. A spike is attached to each pivot for cementing within the respective bone. The design is intended to minimize the transfer of stresses from one component to the other.

U.S. Pat. No. 5,376,121 discloses a dual constraint elbow prosthesis. The prosthesis includes humeral and ulnar members consisting of a spike for insertion into the bone, and the yoke for connecting to a connecting link. The spikes are intended to be secured with cement. The pivot dimensions for the ulnar member are intended to permit a slight sideways rocking, while the humeral member is more constrained. The prosthesis permits 16° of varus and valgus laxity as well as 10° of rotational laxity between the humeral and ulnar components with the hope that this would decrease polyethylene wear. Pivotal rotation that decreases torque is described. By using two axes of rotation, this design reproduces the anterior translocation of the ulna during motion.

U.S. Pat. No. 5,458,654 discloses a screw fixed femoral component for a hip joint prosthesis. The prosthesis includes an intramedullary stem as well as a portion for receiving a ball head. The stem has lateral screw holes defined therein. The stem is secured to the bone by drilling holes into the bone corresponding to the screw holes in the stem, and then driving screws into these holes.

U.S. Pat. No. 5,667,510 discloses a system for fusing the middle and distal phalanx bones in the finger.

U.S. Pat. No. 5,723,015 discloses an elbow prosthesis. The prosthesis includes an ulnar component having a head for receiving the spindle of the humeral components. A ring-like clip retains the spindle within the head. Both components have stems that are cemented into the intramedullary canal. Some play is permitted between the spindle and the clip.

U.S. Pat. No. 5,782,923 discloses an endoprosthesis for an elbow joint. The endoprosthesis includes hingedly connected humeral and ulnar components, each of which having a shaft for engagement in the bone canal. The ulnar component includes a lateral flange having a socket for guiding a sliding member. A radial component has a head portion that is swingingly mounted in the sliding member, thereby providing ball and socket articulation. The radial portion is, therefore, both swingable and displaceable with respect to the ulnar portion. The stems for the humeral, ulnar and radial components are cemented.

U.S. Pat. No. 5,879,395 discloses a total elbow prosthesis. The prosthesis includes cooperating humeral and ulnar elements. A radial element is provided with a ball that fits within a concave surface defined within the humeral element.

U.S. Pat. No. 6,027,534 discloses a modular elbow. The elbow includes humeral and ulnar components having stems for implantation in the intramedullary canals of the respective bones, and body portions that are each designed to receive bearings. The humeral member includes a pair of arms with a pivot extending therebetween, upon which one of the bearings may be placed. The ulnar member includes a slot for receiving a bearing member. The elbow may be used in an unconstrained manner by placing a generally cylindrical bearing on the humeral portion and a bearing having a concave surface on the ulnar portion. Alternatively, the implant may be used in a constrained manner by using a single bearing connected to both the humeral and ulnar components. A similar device is disclosed in U.S. Pat. Nos. 6,290,725 and 6,699,290.

U.S. Pat. No. 6,126,691 discloses a bone prosthesis fixation device. The mechanism includes a main body for implantation within the canal of a bone. The main body includes an internal passageway, as well as a plurality of openings extending between the passageway and the exterior of the main body. A plurality of bone engaging members are reciprocally positioned within each opening. When a plunger is passed into the internal passageway, the bone engaging members are pushed outward, thereby engaging the bone and securing the prosthesis into the bone. A second embodiment also provides a prosthetic device implantable into skeletal bone and has an elaborate gear system that rotates screws that gain fixation into the intramedullary canal.

U.S. Pat. No. 6,162,253 discloses a total elbow arthroplasty system that is intended for use in dogs, but for which the patent also recites possible use in humans. The device includes a combined radio-ulnar component having stems for installation into the canals of both the radius and the ulna. A concave surface on this component mates with a convex surface on the humeral components.

U.S. Pat. No. 6,306,171 discloses a total elbow arthroplasty system that is intended primarily for use in dogs, but for which the patent also recites possible use in humans. The implant includes a radial component having an isometric ball component that fits within a corresponding humeral component to form an unconstrained joint.

U.S. Pat. No. 6,379,387 discloses an elbow prosthesis. The elbow prosthesis includes a humeral component having a substantially cylindrical articulating surface that is concave, with its narrowest portion near the center of the part that interacts with the ulnar component. An ulnar component includes a second articulating surface having a concave portion structured to articulate with the humeral component, and having a convex surface to correspond to the surface of the cylindrical articulating surface. Varus and valgus movement is, therefore, permitted while retaining contact between the humeral and ulnar articulating surfaces. The ulnar component further includes a locking element forming an additional articulating surface, so that the total articulating surface of the ulnar component can extend over more than 180° of the humeral articulating surface. The locking element may be omitted if the surgeon realizes that the tendons and ligaments of the joint are in good condition. A portion of the humeral component's articulating surface extends beyond the retaining arms and interfaces with a radial component. A similar elbow prosthesis is disclosed in U.S. Pat. No. 6,760,368.

U.S. Pat. No. 6,475,242 discloses a plastic joint assembly. The joint assembly includes a flexible U-shaped connector that is secured to adjacent bones by threaded connectors.

U.S. Pat. No. 6,514,288 discloses a prosthetic femoral stem with a strengthening rib.

U.S. Pat. No. 6,517,541 discloses an axial intramedullary screw for the ostia synthesis of long bones. The screw is used for connecting pieces of fractured bones. The screw includes two tips at opposing ends for interfacing with a screwdriver, and threads across the remainder of its length for cutting into the cortical bone of the medullary canal. The screw can be threaded into one portion of a bone fragment and then, after connecting another bone fragment at the fracture site, screwed in the opposite direction into the second fragment.

U.S. Pat. No. 6,716,248 discloses a prosthetic joint that may be utilized to form either a single axis joint or a double axis joint, permitting the surgeon to decide which type to construct from the kit once the elbow has been exposed during surgery. A similar device is disclosed in U.S. Pat. No. 6,997,957.

U.S. Pat. No. 6,890,357 discloses an elbow prosthesis similar to that of U.S. Pat. No. 6,379,387. The elbow prosthesis includes a humeral component having a substantially cylindrical articulating surface that is concave, with its narrowest portion near the center of the part that interacts with the ulnar component. An ulnar component includes a second articulating surface having a concave portion structured to articulate with the humeral component, and having a convex surface to correspond to the surface of the cylindrical articulating surface. Varus and valgus movement is, therefore, permitted while retaining contact between humeral and ulnar articulating surfaces. The ulnar component further includes a locking element forming an interconnection with an additional articulating surface, so that the total articulating surface of the ulnar component can extend 360°. The locking element may be omitted if the surgeon realizes that the tendons and ligaments of the joint are in good condition. A portion of the humeral component's articulating surface extends beyond the retaining arms, and interfaces with a radial component or native radial head.

U.S. Pat. No. 7,247,170 discloses an elbow prosthesis. The ulnar component includes a pair of concave spherical bearing surfaces that interface with a pair of convex spherical bearing surfaces on the humeral components. An axis passing through the ulnar component connects the two bearing surfaces of the humeral components. The spherically shaped bearing surfaces are intended to transmit load over a relatively large area rather than at a point or over a line of contact. The surgeon may employ a modular flange for compressing a bone graft, a tissue fastener for securing soft tissue to a portion of the prosthetic joint, a cam for limiting the amount by which the prosthetic joint articulates or a bearing insert for tailoring the degree of varus/valgus constraint.

U.S. Pat. No. 7,850,737 discloses a prosthetic elbow replacement. The elbow replacement includes a humeral component having a stem dimension to fit within a medullary canal of a humorous, as well as a J shaped flange for providing additional support of the implant with respect to the humerus. Both the stem and the J shaped flange include porous surface sections into which bone tissue can grow and/or bone cement can infiltrate. The humeral component also includes a yoke terminating in a pair of arms having a pivot connected therebetween. The pivot includes a through hole for use in attaching an ulnar component. The ulnar component also includes an ulnar stem having a porous surface portion. Varus and valgus motion is provided by movement of the ulnar component with respect to the through hole of the pivot.

US 2005/0049710 discloses a prosthesis for partial replacement of an articulating surface on bone. The surfaces that are to be replaced are for the coronoid and the radial head. The fixation of these partial prostheses is done with headless and regular screws.

US 2007/0185584 discloses a method and apparatus for digit joint arthroplasty. The method includes drilling and tapping the intramedullary canal, and then utilizing a threaded rod to secure the implants in place. The implant is intended to replace the articular surface of the bone with a similarly shaped metal surface, thereby avoiding the use of a hinge joint with a constant center of rotation, and maintaining the mechanical advantage of the flexor and extensor tendons in the same manner as the natural joint structure. Additionally, reproducing normal physiologic motion has the added benefit of limiting the stresses transmitted through the prosthesis to the stem-bone interface.

US 2010/0179661 discloses an elbow prosthesis. The ulnar component includes a pair of concave spherical bearing surfaces that interface with a pair of convex spherical bearing surfaces on the humeral components. An axis passing through the ulnar component connects the two bearing surfaces of the humeral component. The spherically shaped bearing surfaces are intended to transmit load over a relatively large area rather than at a point or over a line of contact. The prosthesis is provided in the form of a joint kit having a plurality of interchangeable bearing inserts which permit the surgeon to tailor the degree of varus/valgus constraint. Some examples can be linked together without fasteners or other hardware.

US 2012/0109322 discloses a prosthesis to replace at least a portion of a comminuted bone fracture. The prosthesis reproduces the articular surface of a comminuted distal humerus fracture in order to restore joint viability and articulation.

From the above description, it is clear that the vast majority of elbow prostheses are secured utilizing bone cement and, therefore, carry all of the inherent disadvantages of bone cement. Of the minority that are secured by screws, the hinge components of many of these implants must be turned along with the threaded shaft, preventing the hinge portion of the implant from being pulled precisely into the correct position and orientation within the bone. Furthermore, threaded attachments are subject to loosening if not further secured by some additional means. Accordingly, there is a need for a mechanical fastener that pivots with respect to the hinge component of the implant, thereby positioning the hinge portion in the correct position at whatever point the mechanical fastener reaches its maximum depth. There is a further need for a threaded or other mechanical attachment for securing implant components to bone that includes both a major loadbearing portion, and a secondary securing portion to ensure the stability of the major loadbearing portion.

Although it is often difficult for a surgeon to know whether a hemiarthroplasty or total arthroplasty will be required prior to commencing surgery, very few of the implants described above may be used for either type of surgery. Accordingly, there is a need for a prosthetic elbow that may be interchangeably used for hemiarthroplasty and total arthroplasty, permitting the surgeon to decide between the two operations mid-surgery.

Numerous methods have been proposed for permitting varus/valgus movements, thereby reducing stresses on the elbow prosthesis as well as the bones to which the prosthesis is attached. However, none of these methods has included any type of ligament reconstruction that would essentially reproduce that which was present in the elbow prior to injury or deterioration. Accordingly, there is a need for an elbow prosthesis that is installed in a manner that includes ligament reconstruction.

All mechanical devices are subject to wear. It is, therefore, helpful to have specific, easily replaceable components that are subject to wear in preference to other, more critical, and more difficult to replace components. Structures which are designed to wear in preference to other structures, and which are easily replaced during simple follow-up surgeries, are therefore needed.

SUMMARY

The above needs are met by a prosthetic joint. One example of the prosthetic joint has a first component having a first intramedullary stem and a first connection portion. The first intramedullary stem is externally threaded and being pivotally secured to the first connection portion. The prosthetic joint further includes a second component having a second intramedullary stem and a second connection portion. The second intramedullary stem being externally threaded and being pivotally secured to the second connection portion. The second connection portion is structured to be movably secured to the first connection portion.

Another example of the prosthetic joint includes a first component having a first intramedullary bone securing portion and a first connection portion. The first connection portion is structured so that it can mate with a natural second bone end or a reconstructed second bone end without modification to the first connection portion.

Yet another example of the prosthetic joint includes a first joint component that is structured for attachment to a first bone. The first joint component being structured to secure a portion of a ligament reconstruction member. The prosthetic joint further includes a second joint component that is structured for attachment to a second bone. The second joint component is structured to secure a portion of a ligament reconstruction member.

A method of installing a prosthetic joint is also provided. One example of the method is carried out by first providing a prosthetic joint having first and second assemblies. The first assembly has a first threaded intramedullary securing member rotatably secured to a first connection portion. The second assembly has a second threaded intramedullary securing member rotatably secured to a second connection portion. The intramedullary canal of the first bone is broached, drilled, and tapped. The first threaded intramedullary securing member is installed into the intramedullary canal of the first bone. The first threaded intramedullary securing member is used to draw the first connection portion into the intramedullary canal of the first bone. The intramedullary canal of the second bone is broached, drilled, and tapped. The second threaded intramedullary securing member is installed into the intramedullary canal of the second bone. The second threaded intramedullary securing member is used to draw the second connection portion into the intramedullary canal of the second bone.

Another example of the method of installing a prosthetic joint between a first bone and a second bone begins by attaching a first joint component to the first bone. A second joint component is attached to the second bone. At least one tendon is removed. A portion of the tendon is secured to the first joint component. Another portion of the tendon is secured to the second joint component.

These and other aspects of the invention will become more apparent through the following description and drawings.

BRIEF DESCRIPTION OF THE DRAWINGS

Like reference characters denote like elements throughout the drawings.

DETAILED DESCRIPTION

Figure 1:
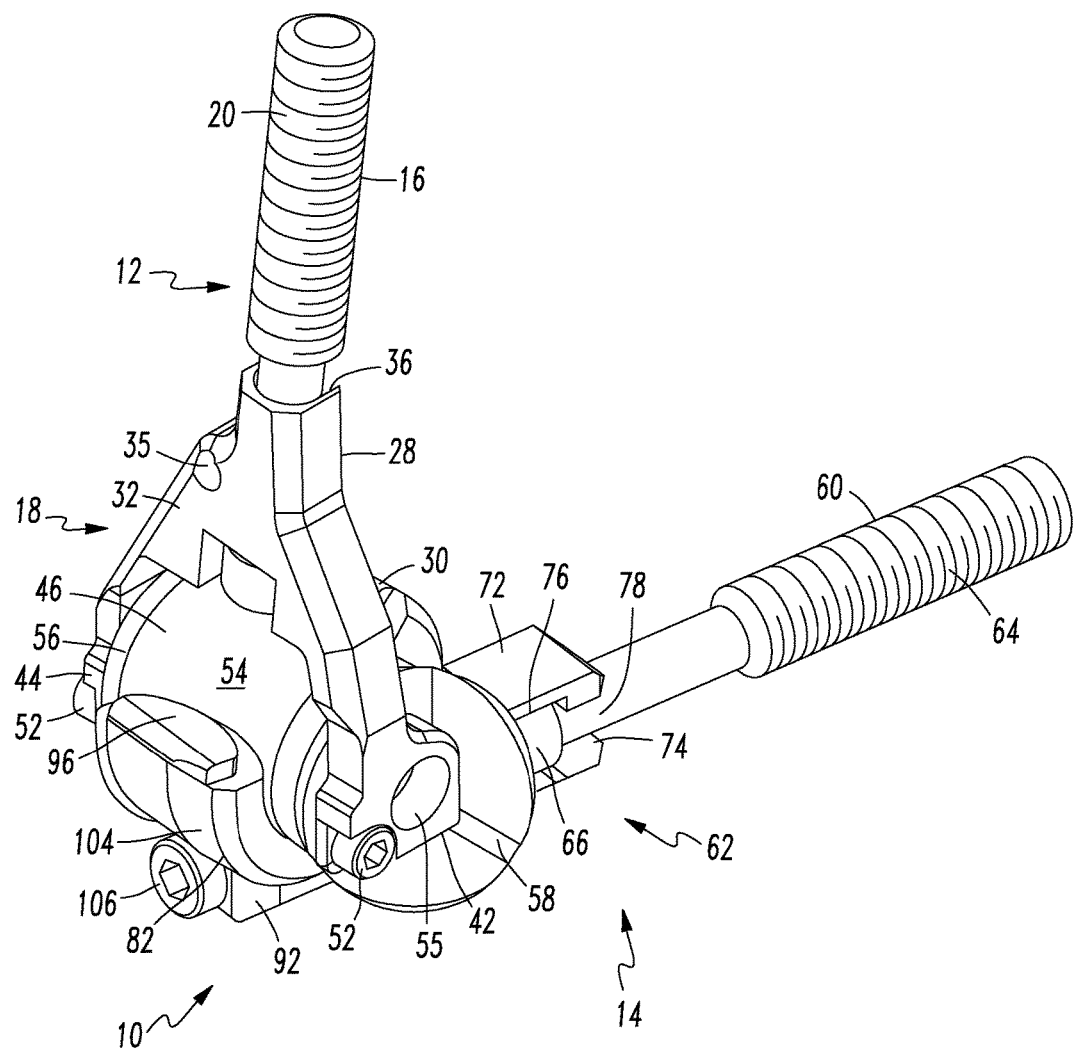
FIG. 1 is an isometric view of a prosthetic joint.
Figure 2:
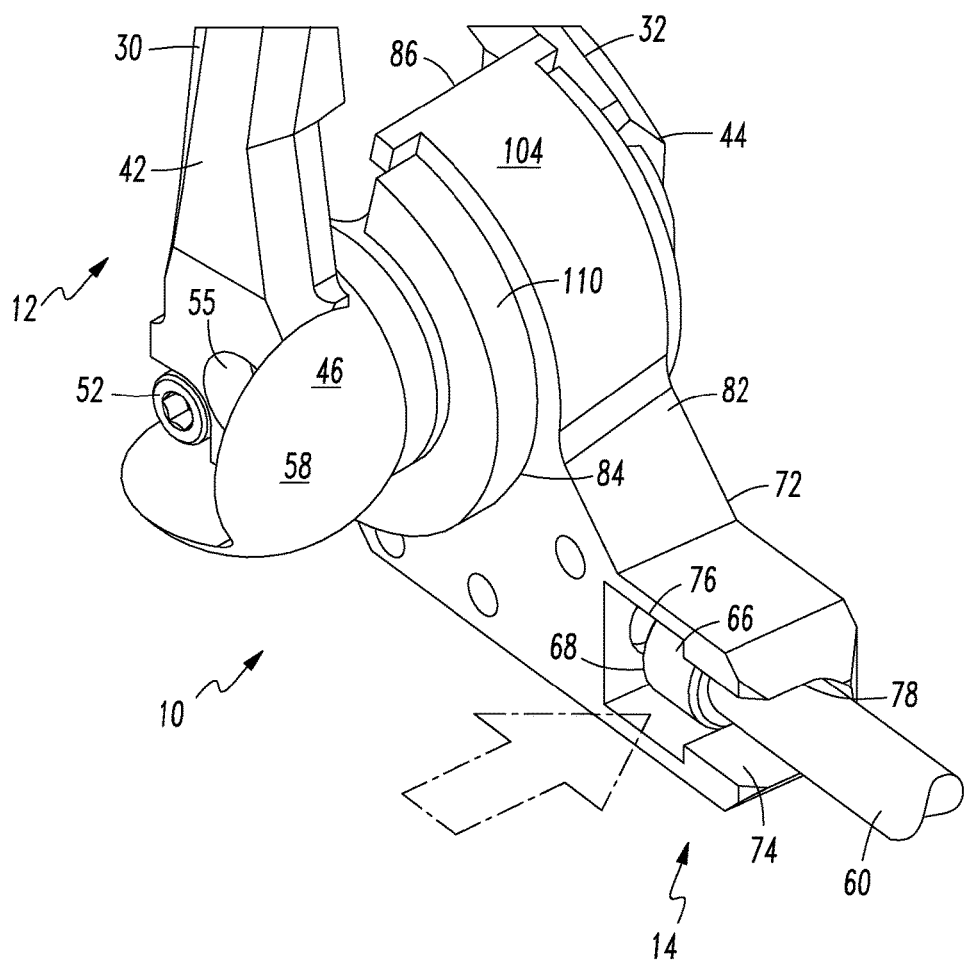
FIG. 2 is an isometric view of the hinge portion of a prosthetic joint.

Referring to the drawings, an example of a prosthetic joint 10 is illustrated. As shown in FIG. 1, the illustrated example of the prosthetic joint 10 is a hinge joint, with the specific example illustrated being an elbow joint. The prosthetic joint 10 includes a first component 12, which in the illustrated example is a humeral component utilized for reconstruction of the distal end of a humerus. The prosthetic joint 10 further includes a second component 14, which in the illustrated example is an ulnar components for use in reconstructing the proximal end of an ulna.

The humeral component 12 includes an intramedullary stem 16 that is rotatably and removably secured to a connection portion 18. The intramedullary stem 16 is structured for uncemented, mechanical securing within the intramedullary canal of the humorous. The illustrated example of the intramedullary stem 16 includes a threaded portion 20 disposed at one end, that is structured to engage a portion of the intramedullary canal that has been tapped with corresponding threads as described in greater detail below. The opposite end of the intramedullary stem 16 includes a head 22, which in the illustrated example has a slightly larger diameter than the immediately adjacent portion of the intramedullary stem 16. The tip 24 of the head 22 includes actuator engaging structures 26 that are structured to engage a rotatable actuation school. For example, the actuator engaging structures 26 could be a slot for a slotted screwdriver, a cross shaped slot for a Phillips head screwdriver, a hexagon shaped hole for an Allen wrench, a star shaped hole for a Torx screwdriver, or any other conventional actuator engaging structure.

Figure 3:
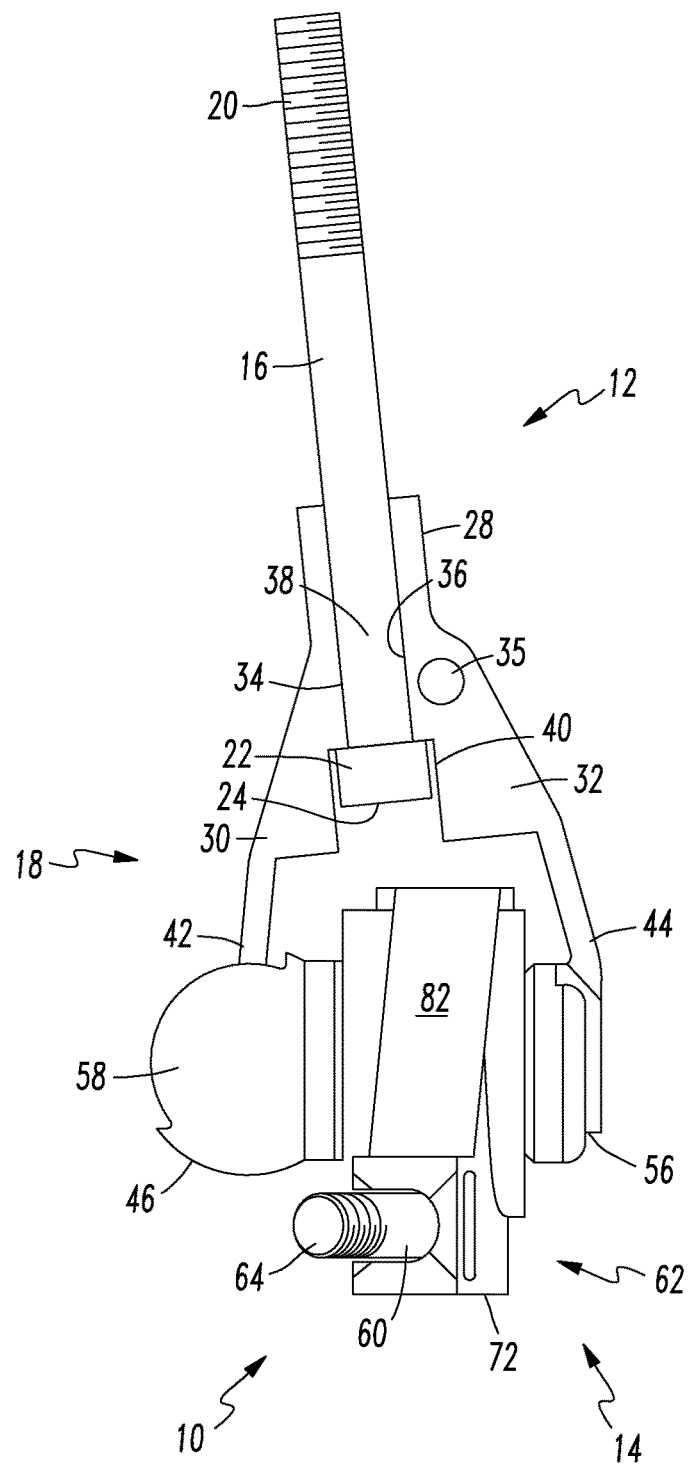
FIG. 3 is a side view of the prosthetic joint.

Referring to FIGS. 1-4 and 22, the connection portion 18 of the humeral component 12 in the illustrated example includes a yoke 28 having first and second legs 30, 32, respectively, extending therefrom. The yoke's base 34 defines a channel 36 therein. As shown in FIG. 3, the channel 36 includes a narrow portion 38 that is a suitable diameter to receive the majority of the intramedullary stem 16, but is too narrow to receive the head 22. The channel 36 further includes a wider portion 40 having a sufficient diameter to receive the head 22. The intramedullary stem 16 may therefore be placed within the channel 36, where it is free to rotate, but where the head 22 is prevented from passing into the narrow portion 38 of the channel 36. A hole 35 is defined within the connection portion 18 for securing a cross locking member 33, as described in more detail below.

The distal ends 42, 44 of the legs 30, 32, respectively are structured to removably secure a spool 46 therebetween. In the illustrated example, openings 48, 50 are defined within the distal ends 42, 44 of the legs 30, 32. The holes 48, 50 are each structured to receive a fastener such as the illustrated screws 52 (FIG. 7) passing therethrough and into corresponding threaded holes 53 defined within the spool 46. The spool 46 is generally cylindrical, and has a generally concave bearing surface 54 extending between its ends. The end 56 of the spool 46 corresponding to the leg 32 is generally flat, and the end 58 of the spool 46 corresponding to the leg 30 is partially spherical. The spool 46 therefore has a shape that generally corresponds to the shape of the distal end of an undamaged humerus. A central bore 53 passes through the spool 46, with corresponding holes 55, 57 being defined within the distal ends 42, 44 of the legs 30, 32, respectively.

Figure 20:
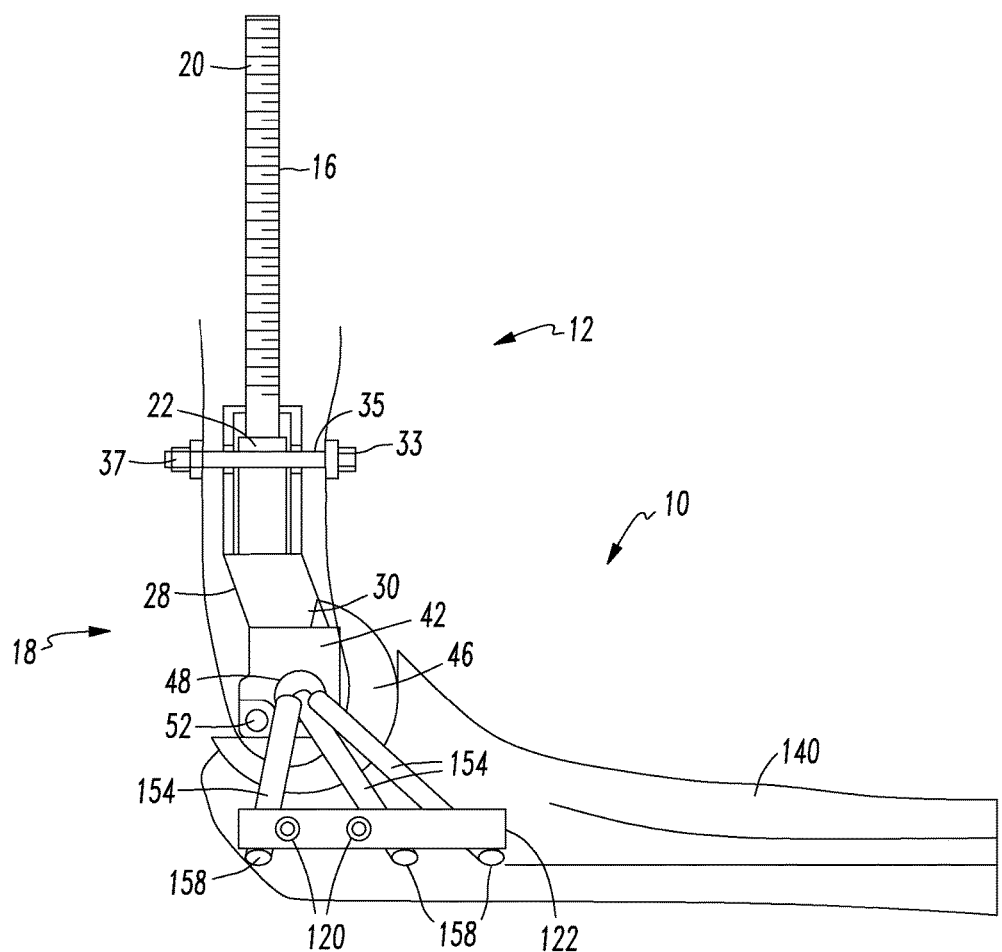
FIG. 20 is a cross-sectional front view of a prosthetic joint after installation for a hemiarthroplasty.
Figure 21:
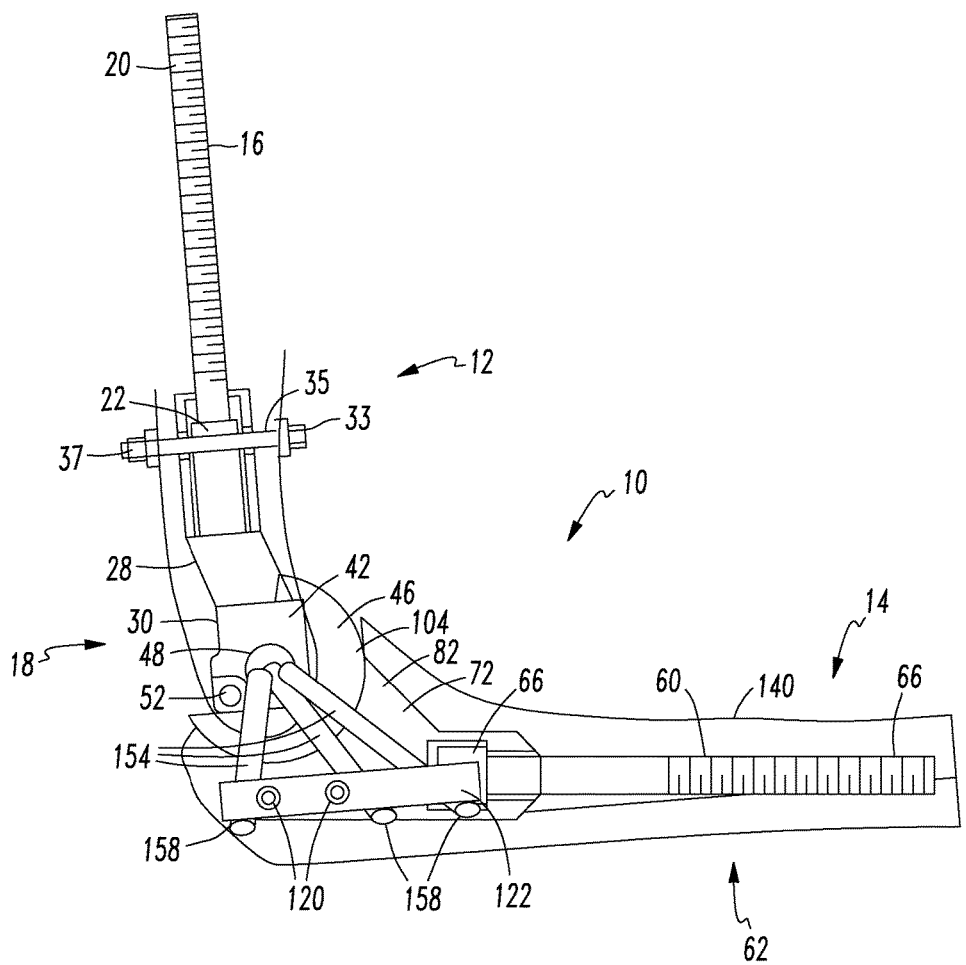
FIG. 21 is a cross-sectional front view of a prosthetic joint after installation for a total arthroplasty.
Figure 22:
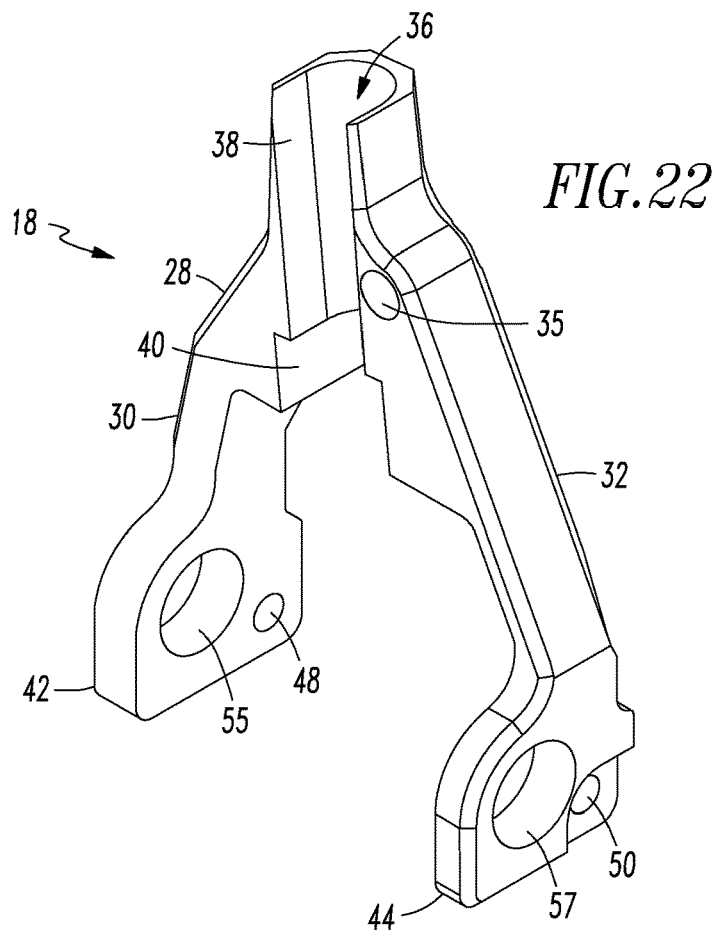
FIG. 22 is an isometric view of a connection portion for a humeral component of a prosthetic joint.
Figure 23:
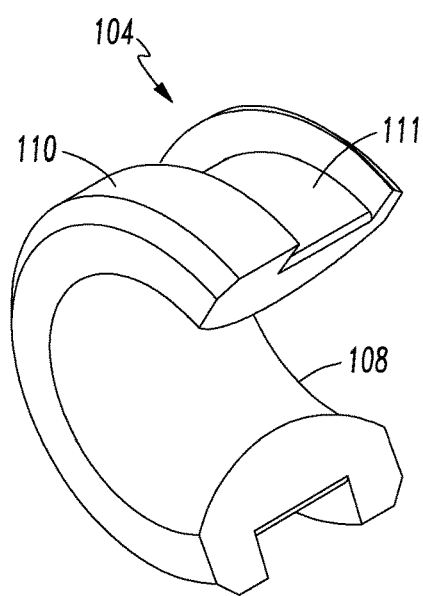
FIG. 23 is an isometric view of a bearing for a prosthetic joint.
Figure 24:
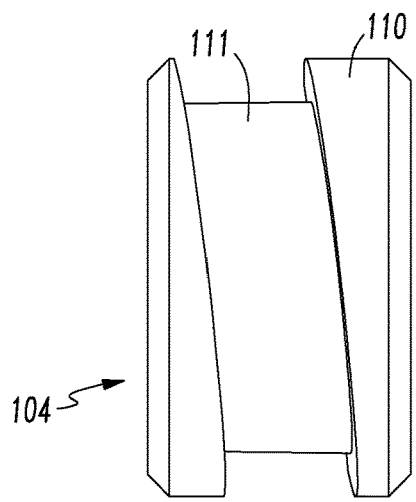
FIG. 24 is a side elevational view of the bearing of FIG. 23.

Referring to FIGS. 20 and 22, the humeral portion 12 includes a cross locking member 33. In the illustrated example, the cross locking member 33 is a screw passing through a corresponding opening 35 defined within the connection portion 12. The screw 33 is secured at the opposite and of the hole 35 by a nut 37.

Referring to FIGS. 1-6, the ulnar component 14 includes in intramedullary stem 60 and a connection portion 62. The intramedullary stem 60 is structured for mechanical, cementless installation into the intramedullary canal of an ulna. In the illustrated example, the distal end 64 of the intramedullary stem 60 is threaded, so that it may engage corresponding threads that have been tapped into the ulna intramedullary canal. The proximal end of the intramedullary stem 60 includes a head 66, having a larger diameter than adjacent portions of the intramedullary stem 60. The tip 68 of the head 66 includes actuator engaging structures 70 that are structured to engage a rotatable actuation school. For example, the actuator engaging structures 70 could be a slot for a slotted screwdriver, a cross shaped slot for a Phillips head screwdriver, a hexagon shaped hole for an Allen wrench, a star shaped hole for a Torx screwdriver, or any other conventional actuator engaging structure.

The connection portion 62 includes a base 72. The base 72 defines a channel 74 therein. The channel 74 includes a narrow portion 76 that is structured to receive the intramedullary stem 60, but not the head 66. A wider portion 78 of the channel 74 is structured to receive the head 66. The intramedullary stem 60 may therefore be placed within the channel 74, and rotatably secured therein, in a manner that prevents the head from passing into the narrow portion 76. The illustrated example includes a threaded hole 80 which, in the illustrated example, is coaxial with the channel 74, and whose purpose will be explained below.

Figure 5:
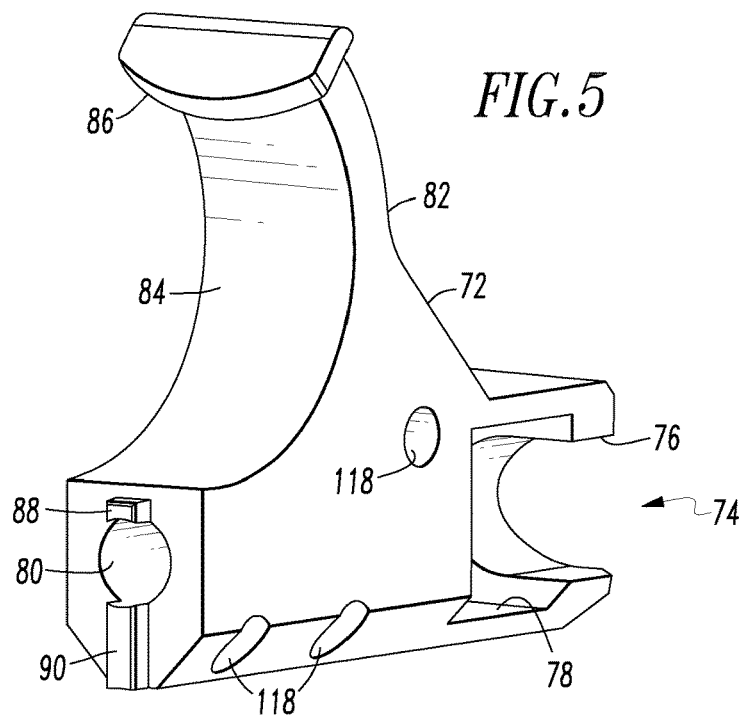
FIG. 5 is an isometric view of a base for a connection portion of a second joint components for a prosthetic joint.
Figure 6:
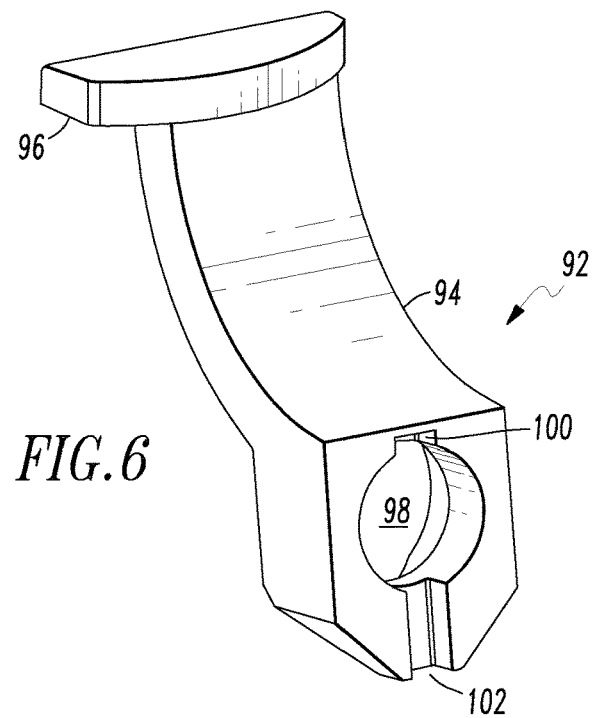
FIG. 6 is an isometric view of a bearing retaining bracket.

The connection portion 72 further includes a bearing retention structure 82. The bearing retention structure 82 includes a concave, generally circular interior surface 84. A bearing retaining flange 86 is disposed at one and of the interior surface 84. The other end of the interior surface 84 terminates adjacent to the threaded hole 80. Referring specifically to FIGS. 5-6, a pair of locating flanges 88, 90 are disposed on either side of the threaded hole 80. A bearing retaining bracket 92, which is best illustrated in FIG. 5, defines a generally circular surface 94 that is structured to form a continuation of the surface 84, and terminating in a bearing retaining flange 96. The opposite end of the bracket 92 defines a hole 98 therethrough, corresponding to the threaded hole 80. A pair of slots 100, 102 on either side of the hole 98 correspond to the locating flanges 88, 90, respectively, facilitating precise placement of the bracket 92 in the desired location. With the bracket in this position, a bearing 104 may be retained by the connection portion 14. A screw 106 passing through the hole 98 and engaging the threaded hole 80 secures the bearing retaining bracket 92 to the base 72.

Referring to FIGS. 1-4 and 23-24, the bearing 104 is generally half doughnut shaped, defining an interior, generally semicircular surface 108, and an exterior, generally semicircular surface 110. The bearing 104 preferably extends around at least about half of the spool 46, but defines a sufficient opening to allow for easy installation of the bearing 104 on the spool 46, for example, within a range of about 180° to about 270°. The bearing 104 in the illustrated example extends around about 236°. The interior surface 108 is generally convex, having a shape corresponding to the shape of the spool 46. The exterior surface 110 defines a channel 111 therein for receiving the bearing retention structure 82 as well as the bracket 92. The channel 111 is angled with respect to the circumference of the bearing 104 to accommodate the angle made by the bearing 104 with respect to the ulnar component 14, which in the illustrated example is about 7°. The retaining flanges 86, 96 are wider than the channel 111 so that the bearing 104 is properly retained. The bearing 104 is preferably made from a material having a wear resistance that is less than the wear resistance of the components with which it interfaces, so that the bearing 104 will experience wear in preference to other portions of the prosthetic joint. In the illustrated example, the bearing 104 is preferably made from polyethylene.

Referring to FIGS. 17-20, a cross locking assembly 114 for the ulnar component 14 is illustrated. The cross locking assembly 114 includes a plurality of cross locking members 116, which in the illustrated example are screws. The cross locking screws 116 pass through corresponding holes 118 (FIG. 4) defined it within the base 72, and are retained by corresponding nuts 120 disposed on the opposite sides of the holes 118. The screws 116 and nuts 120 also retain the bars 122, 124 in place against the base 72, for a purpose that will be described in greater detail below.

Figure 7:
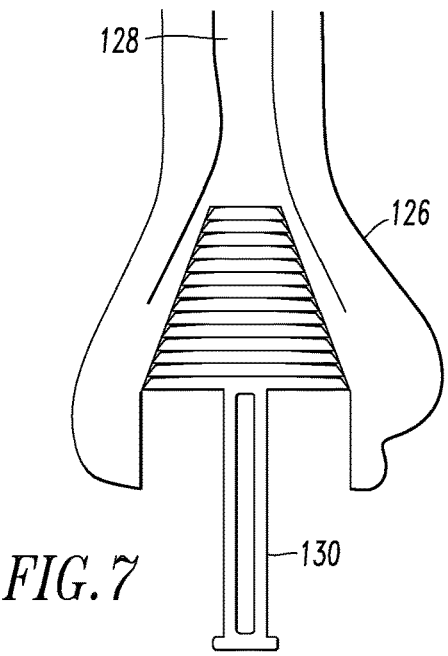
FIG. 7 is a cross-sectional side view of a broaching process for installation of a prosthetic joint component.

A method of installing the first joint component within the first bone (installing the humeral portion within the distal end of the humerus 126 in the illustrated example) is illustrated in FIGS. 7-11. This method remains the same regardless of whether a hemiarthroplasty or total arthroplasty is being performed. Initially, the damaged distal end of the humerus is cut with a saw. Next, as illustrated in FIG. 7, the intramedullary canal 128 is broached to remove marrow, as well as to provide adequate room for a drilling jig, as well as ultimately for the humeral implant 12. In some examples, three different sizes of brooches 130 may be utilized.

Figure 8:
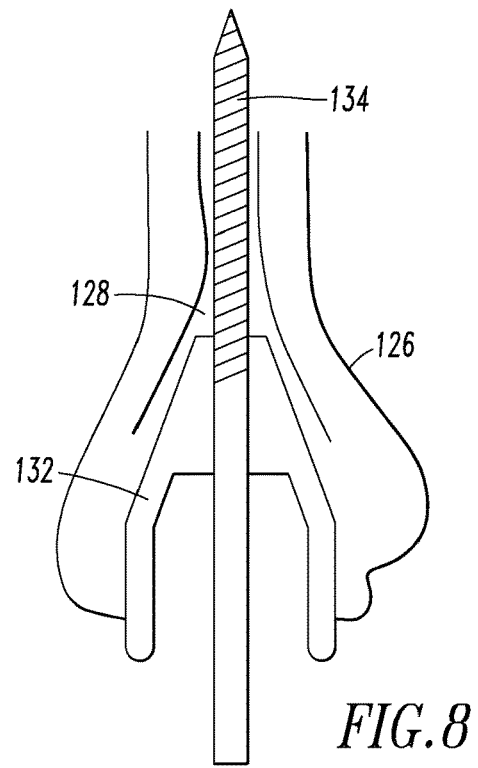
FIG. 8 is a cross-sectional side view of a drilling process for installation of a prosthetic joint component.
Figure 9:
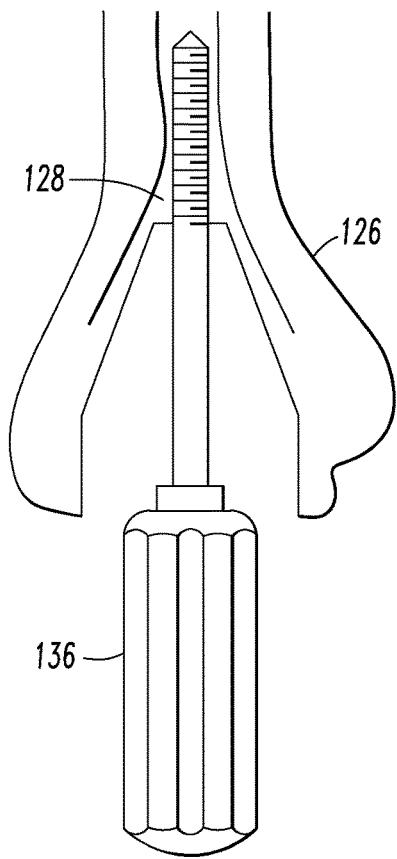
FIG. 9 is a cross-sectional side view of a tapping process for installation of a prosthetic joint component.

As shown in FIG. 8, a jig 132 is inserted into the intramedullary canal 128, and is used to guide a drill 134 in further clearing the marrow from the intramedullary canal 128. Successively larger drill bits are used until proprioceptive and or audible indications of drilling solid bone are heard. Once solid bone has been reached, the intramedullary canal 128 is tapped using a handheld tap 136, as shown in FIG. 9, thereby providing threads corresponding to the threads 20 of the intramedullary stem 16.

Figure 10:
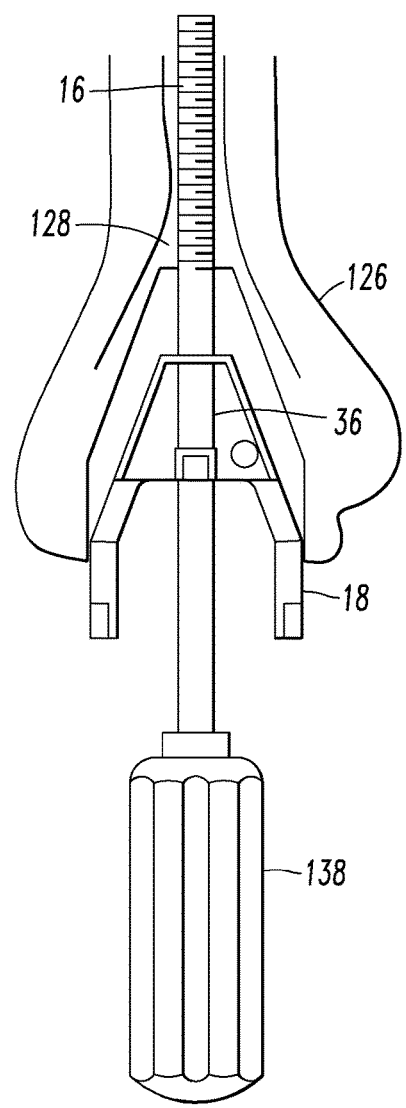
FIG. 10 is a cross-sectional side view of a prosthetic joint component being installed within a bone.

Referring to FIG. 10, an appropriately sized intramedullary stem 16 and connection portion 18 are selected. It is anticipated that different sizes of intramedullary stem 16 and connection portion 18 may be provided, thereby accommodating patients of different sizes. Because the intramedullary stem 16 is removably secured to the connection portion 18, the appropriate combination of parts may be selected. The intramedullary stems 16 is placed within the channel 36, and is then threaded until secured within the intramedullary canal utilizing an appropriate screwdriver 138 or other suitable hand tool. Because the intramedullary stem 16 is rotatable with respect to the connection portion 18, the connection portion 18 remains in the appropriate position for proper seating within the distal humerus 126 well-being drawn tightly into place by turning the intramedullary stem 16. During this operation, the spool 46 is detached from the connection portion 18 in order to facilitate access by the tool 138.

Figure 11:
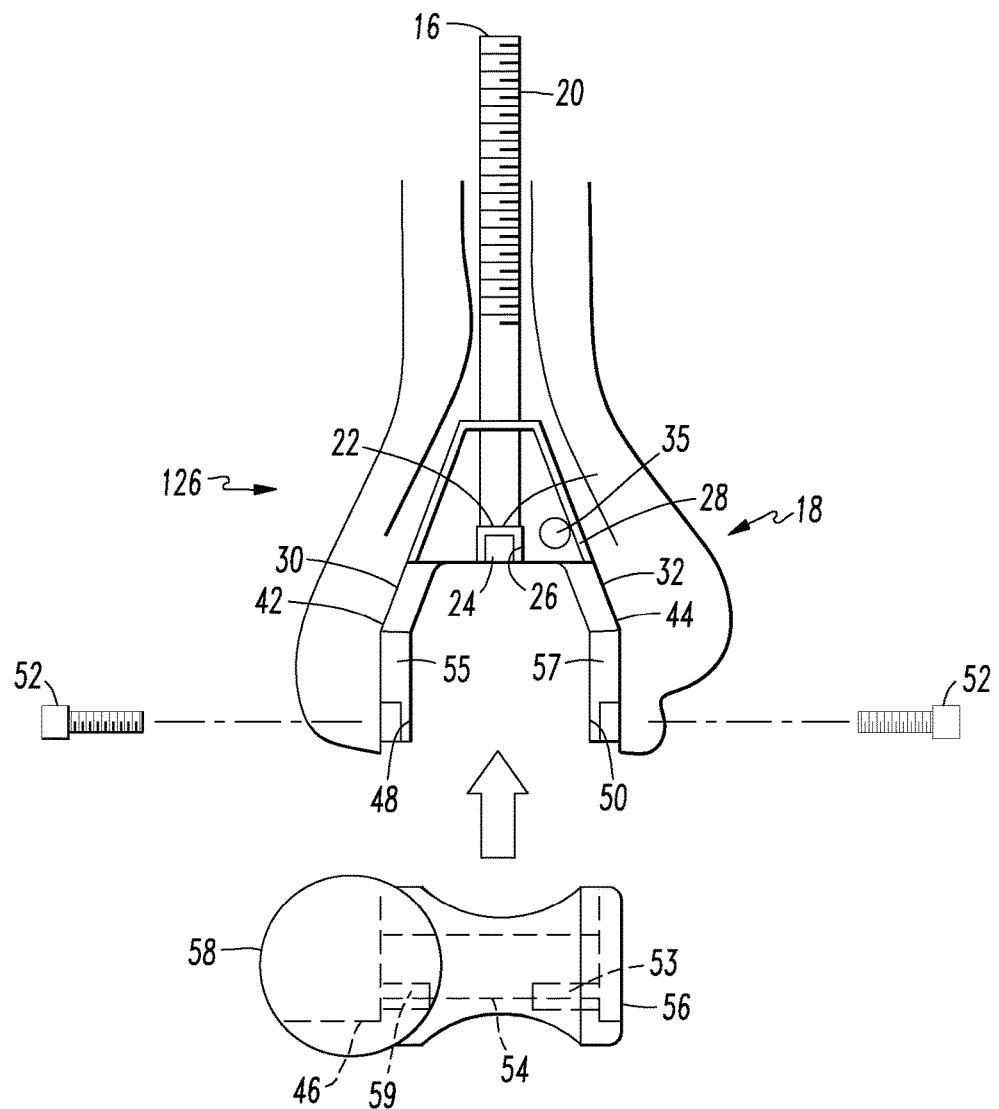
FIG. 11 is a cross-sectional side view of a spool for a prosthetic joint component being installed.

Once the connection portion 18 is firmly seated in place, as shown in FIG. 11, a hole corresponding to the hole 35 is drilled into the humerus 126, and the cross locking screw 33 is inserted into the hole 35. The nut 37 is added to complete the humeral cross locking structure. Next, the spool 46 is positioned between the legs 30, 32, and secured in place using the screws 52. At this point, the end is surface of the distal humerus 126 has been restored, and may be utilized for either a hemiarthroplasty utilizing an undamaged proximal ulna, or a total arthroplasty by installing an ulnar component as described below.

Figure 12:
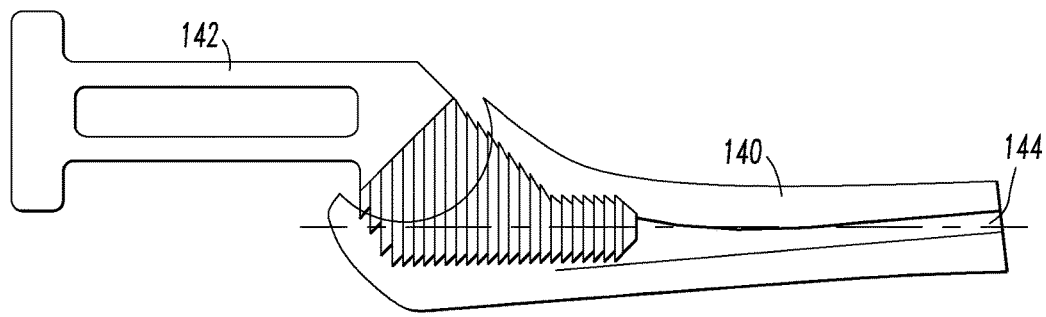
FIG. 12 is a cross-sectional front view of a broaching process for installation of a prosthetic joint component.
Figure 13:
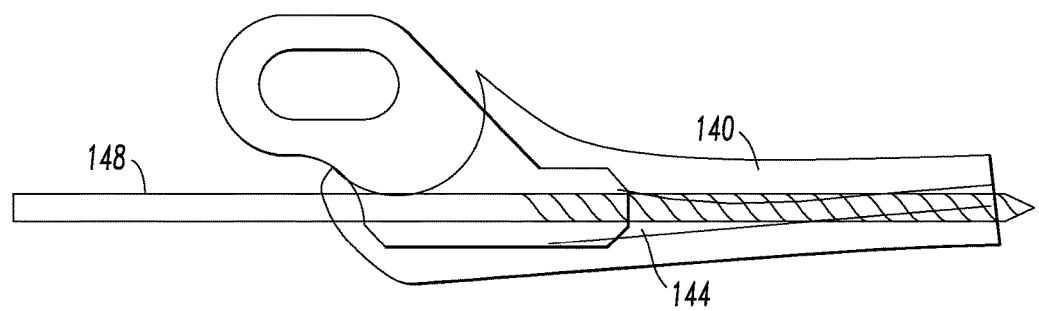
FIG. 13 is a cross-sectional front view of a drilling process for installation of a prosthetic joint component.
Figure 14:
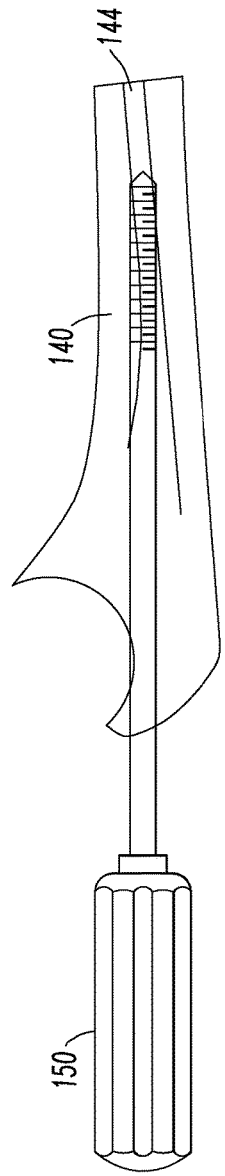
FIG. 14 is a cross-sectional front view of a tapping process for installation of a prosthetic joint component.

Referring to FIGS. 12-16, a method of installing the ulnar joint portion 14 is illustrated. Initially, the proximal end of the ulna 140 is broached utilizing a hand-held broach 142 to remove marrow from the intramedullary canal 144, as shown in FIG. 12. Next, a jig 146 is positioned within the proximal end of the intramedullary canal 144 to guide a drill 148 into the intramedullary canal 144 as shown in FIG. 13. Successively larger drill bits 148 are utilized until the marrow has been removed from a portion of the intramedullary canal to be tapped, and proprioceptive or audible indications that solid bone has been engaged are felt or heard. At this point, the intramedullary canal is tapped as shown in FIG. 14 by a handheld tap 150 to produce threads corresponding to the threads and 64 of the intramedullary stem 60. At this point, the ulna 140 is prepared for installation of the prosthetic joint portion 14.

Figure 15:
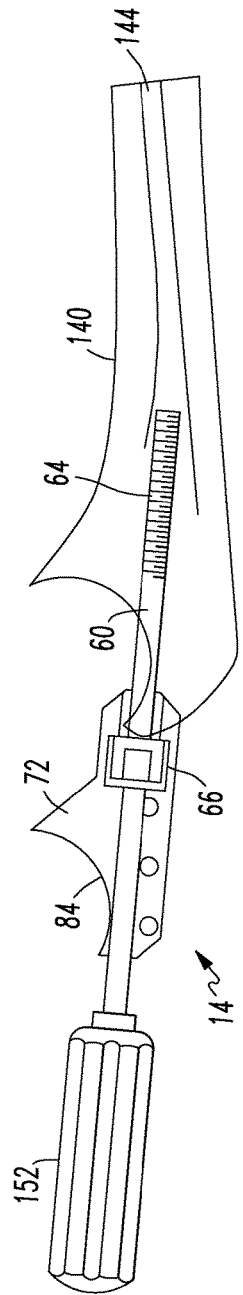
FIG. 15 is a cross-sectional front view of a prosthetic joint component being installed within a bone, showing the prosthetic joint component partially installed.
Figure 16:
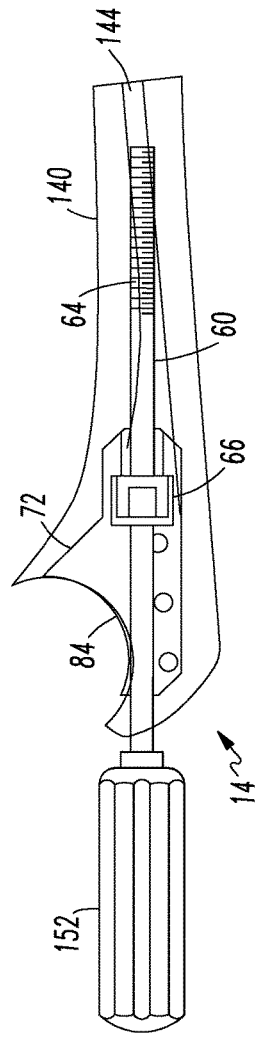
FIG. 16 is a cross-sectional front view of a prosthetic joint component being installed within a bone, showing the final position of the prosthetic joint component.

An appropriately sized intramedullary stem 60 is paired with an appropriately sized base 72, as shown in FIG. 15. Different sized, interchangeable intramedullary stems 16 and bases 72 may be selected depending on the characteristics of the patient. The intramedullary stem 60 is placed within the channel 74, and the threads 64 are brought into engagement with the threads that were tapped into the intramedullary canal 144. An appropriate tool, which in the illustrated example is the screwdriver 152, is inserted into the threaded hole 80 and brought into engagement with the actuator engaging structures 70 within the head 66 of the intramedullary stem 60. The screwdriver 152 is turned to pull the prosthetic joint portion 114 into the ulna 140. Because the intramedullary stem 60 is rotatable with respect to the base 72, the base 72 may remain in a proper orientation as the intramedullary stem 60 is turned, thereby permitting the turning of the intramedullary stem 60 to draw the base 72 tightly into position within the ulna, as shown in FIG. 16.

Figure 4:
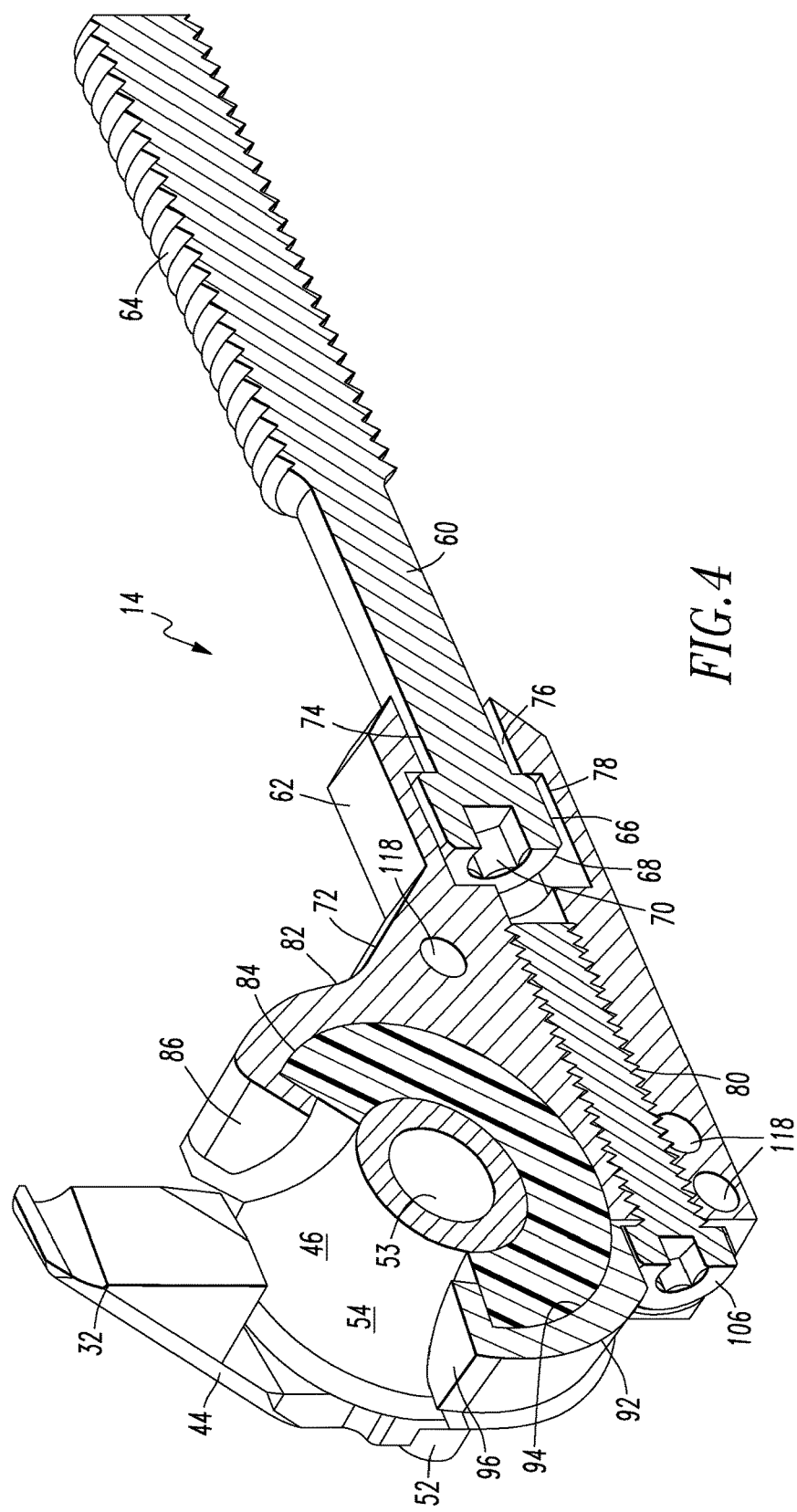
FIG. 4 is a partially cutaway isometric view of a second prosthetic joint component, showing the second prosthetic joint component engaging a spool attached to a first prosthetic joint component.

Once the prosthetic joint component 14 has been installed within the ulna, a bearing 104 is placed against the interior surface 84 of the base 72 (FIGS. 4-6). The bearing retaining bracket 92 is positioned against the base 72. The screw 106 is then secured within the threaded hole 80, thereby securing the bracket 92 and bearing 104 in position within the prosthetic joint component 14. At this point, the prosthetic joint components 12, 14 are ready to be joined together. Also, at this time, holes are drilled in the ulna 140 to correspond to the holes 118 in the base 72.

Regardless of whether hemiarthroplasty or total arthroplasty is being performed, the illustrated example substantially mimics the movement and stability of a natural joint through a system of ligament reconstruction. Joint stability is defined as the resistance to subluxation under physiologic stress and is the result of the mechanical interaction of the articular contours, the dynamic support of the investing musclotendinous units, and the static viscoelastic constraint of the capsuloligatmentous structures. In order to be useful to the patient, the design of the prosthetic joint 10 must preserve this stability. Given that this design aims to replicate the native elbow bony anatomy and does not utilize a mechanical hinge to resist varus and valgus forces, the stability requirements are placed on the soft tissues.

Collateral ligaments are complex structures whose individual fascicles are under differential tension and whose properties depend on joint position and load. The collateral ligaments of the elbow, by virtue of their medial and lateral locations, have a mechanical advantage in resisting medially and laterally directed forces that would cause joint subluxation. In an effort to gain joint visualization during arthroplasty surgery, these ligaments are detached and then re-inserted once the implants have been placed. Reattachment is difficult to do particularly when the ligament integrity is compromised such as in the joints of elderly patients.

Patients suffering from post-traumatic arthritis often sustained soft tissue as well as bony trauma making a subsequent collateral ligament repair more tenuous. Therefore, tendons taken from the patient or allograft tendons are utilized as ligament reconstruction members, as described below.

Initially, tendons are selected from the patient for use in reconstructing the ligaments. The specific tendon or tendon portion selected are chosen because its loss will have minimal or no impact on the patient. Tendons that may be advantageously utilized include a longitudinal strip of triceps tendon or the Palmaris Longus tendon. Alternatively, toe extensors or the Plantaris tendon or even half of the Flexor Carpi Radialis tendon can be used. Allograft tendon material may also be utilized.

Figure 17:
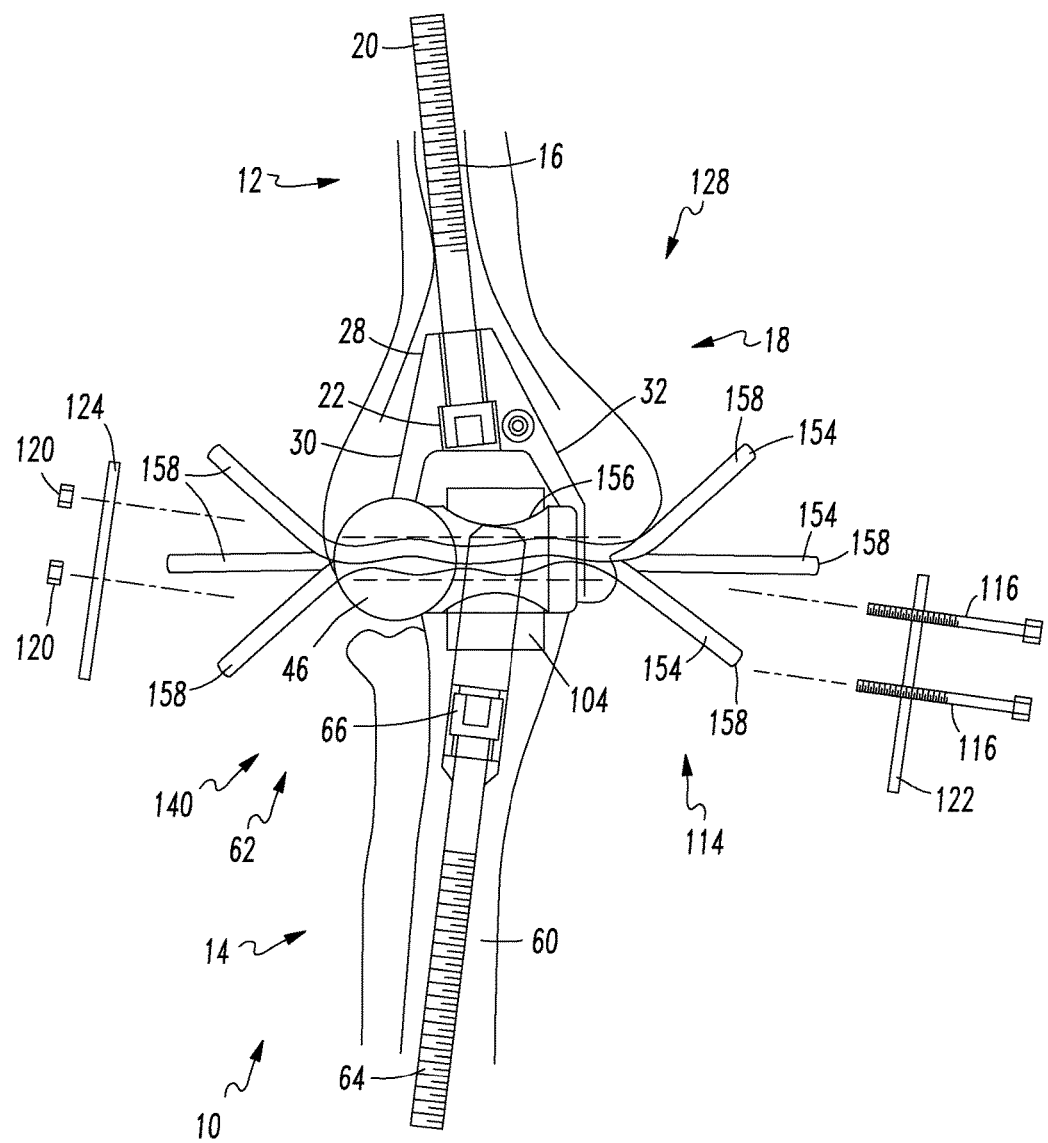
FIG. 17 is a cross-sectional side view showing the insertion of ligament reconstruction members through the first prosthetic joint component.
Figure 18:
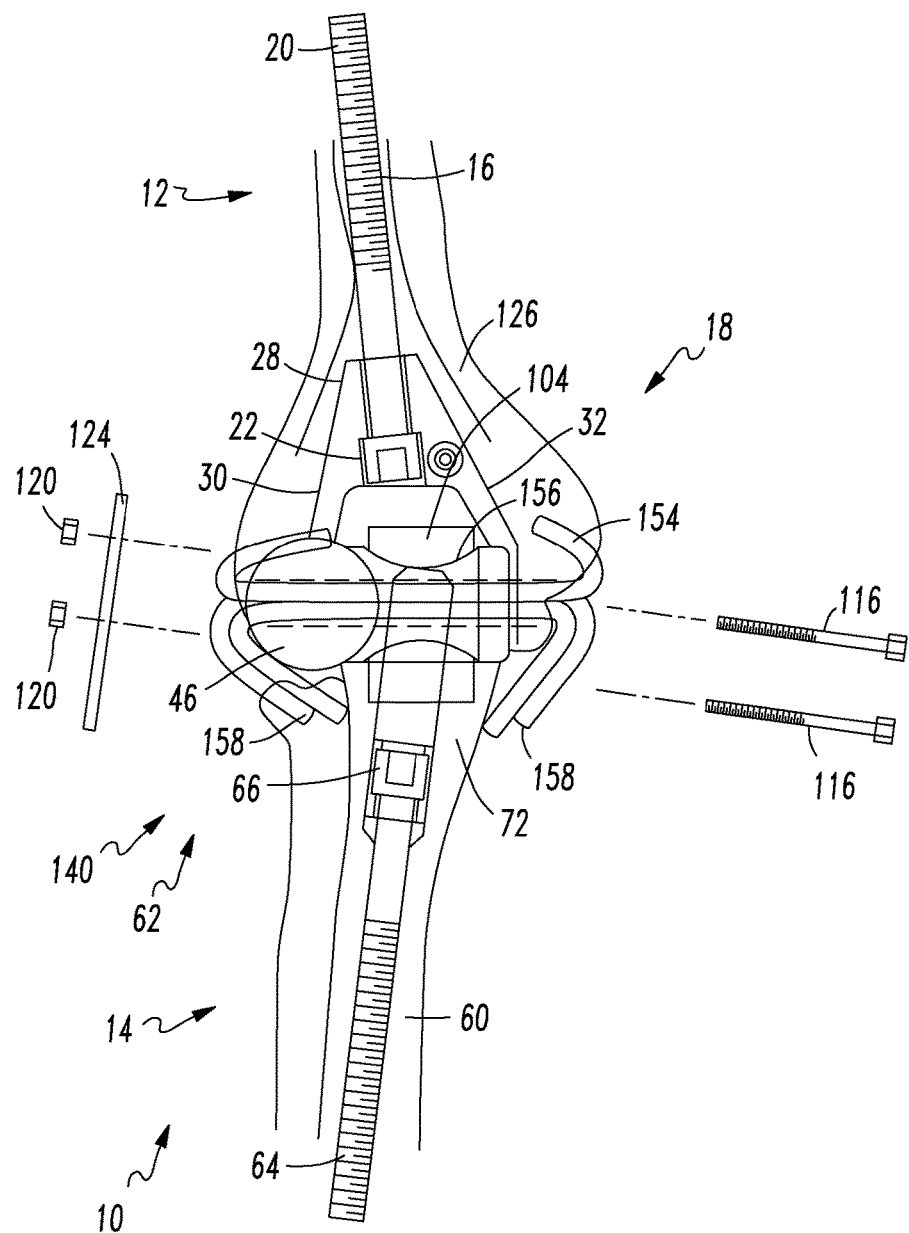
FIG. 18 is a cross-sectional side view showing the attachment of ligament reconstruction members to the second prosthetic joint component, as well as the installation of cross locking members.
Figure 19:
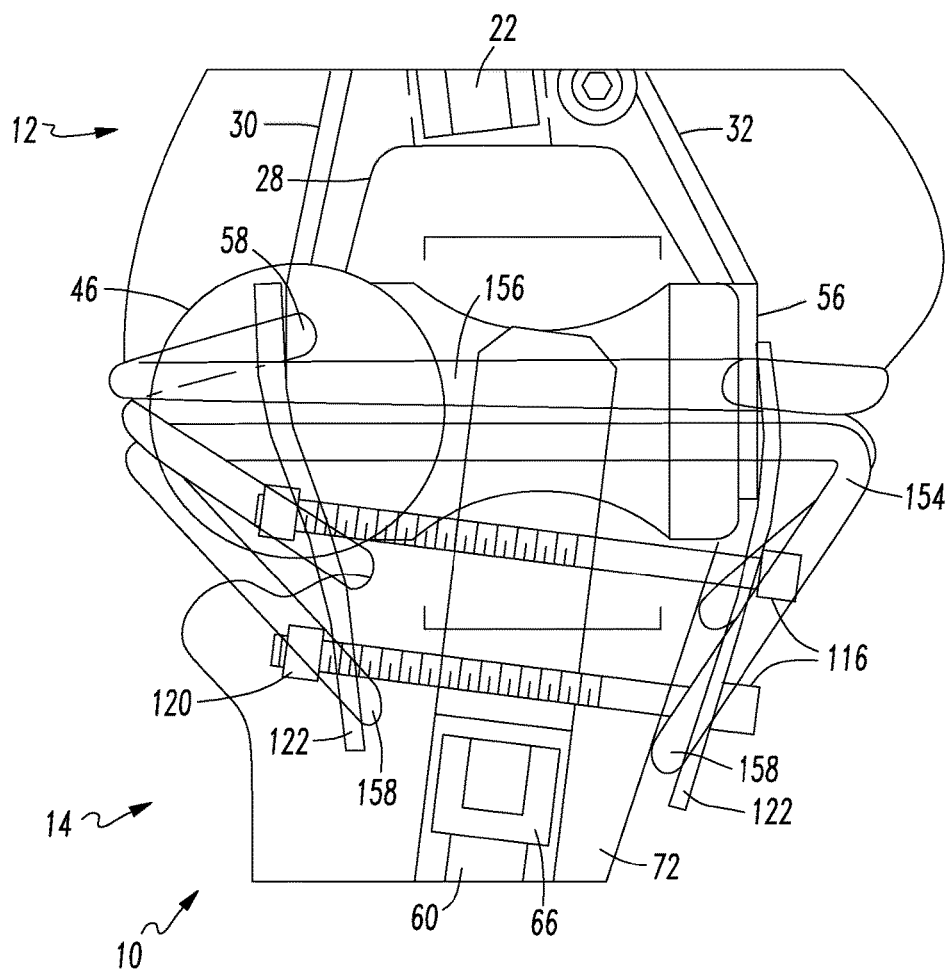
FIG. 19 is a cross-sectional side view of a ligament reconstruction for a prosthetic joint.

With the appropriate ligament reconstruction members 154 obtained, the humeral joint portion 12 and ulna (in the case of hemiarthroplasty) or ulnar joint portion 14 (in the case of total arthroplasty) are placed against each other as shown in FIG. 17. The ulnar articulating surface will be native cartilage if a hemiarthroplasty is being performed, or the bearing 104 if total elbow arthroplasty is being performed. The ligament reconstruction members 154 are utilized to connect the humeral joint portion 12 and ulnar joint portion 14 by securing a portion of the ligament reconstruction members 154 to the humeral portion 12, and another portion of the ligament reconstruction members 154 to the ulnar portion 14. In the illustrated example, a central portion 156 of the ligament reconstruction members 154 is passed through the central bore 53 of the spool 46, as well as the holes 55, 57 defined within the distal ends 42, 44 of the legs 30, 32 of the yoke 28. The end portions 158 of the ligament reconstruction members 154 are then tensioned in order to remove their viscous properties, and secured to either the ulna (in the case of a hemiarthroplasty) or to the base 72 of the ulnar joint component 14 (in the case of a total arthroplasty) by securing the ends of the ligament reconstruction members 154 underneath the plates 122, 124. The plates 122, 124 in the illustrated example are held in place by the cross locking screws 116 and nuts 120, so cross locking of the ulnar component is also accomplished during this step. The tendon to bone fixation is, thereby, accomplished through the creation of compressive force exerted between the ulna and the plate. This method will maintain the appropriate tension within the tendons while bone to tendon healing occurs, and thereby ensures the stability of the reconstructed joint. This design also maintains the dynamic support of the extensor and flexor tendon insertions, which is accomplished by leaving the lateral and medial epicondyles intact.

The prosthetic joint described above provides numerous advantages over the prior art. The present design does not include cement fixation at all, and thereby eliminates the risk of bone cement implantation syndrome, as well as the other disadvantages of using bone cement. It is anticipated that, as the bones heal, they will grow into and/or around the various components of the prosthetic joint, thereby enhancing the security with which the prosthetic joint components are attached to the respective bones. Avoiding bone cement removes the exothermic curing process that may damage bone secondary to thermal osteonecrosis. In the event of infection, removal and replacement of prosthetic joint components is greatly simplified.

The attachment of the prosthetic joint components to the respective bones is particularly secure, and is anticipated to be able to withstand forces imparted to the biomechanical construct in excess of those which could be withstood by prior prosthetic joints. The use of relatively long intramedullary stems increases the surface area against which forces are applied, thereby reducing the pressure applied for an equivalent force. A screw that gains purchase in the threaded intra-medullary canal can pull the implant into the bone and create a very stable intra-medullary fixation based construct by distributing the forces over a sizeable number of threads. By leveraging the length of the humerus and ulna as well as the high cortical to cancellous bone ratio within the middle thirds of the humerus and ulna, the proposed method of fixation will make secure un-cemented implant fixation possible in a safe and reproducible manner. By distributing the forces over multiple threads, fixation through the intra-medullary screw is possible and reproducible even in bone that is fragile as is seen in osteoporotic patients. The use of interchangeable intramedullary stems and connection portions makes it possible to provide different length threaded rods that would not over-penetrate the far cortex beyond where it is achieving fixation. The use of cross locking members resists any tendency of the intramedullary stems to loosen over time.

The prior art method of constraining a total elbow arthroplasty resides in either using a hinge device in the implant (constrained) or repairing the ligaments after elbow replacement (unconstrained). No commercially available or previously marketed design attempts to provide stability through reconstruction of the elbow ligaments. Conversely, in the present design, the elbow is stabilized in a manner that most closely approximates how it functions in vivo. Secure ligament reconstruction is particularly advantageous as the patient populations that frequently receives this type of surgery often suffer from inflammatory arthritis and may not have a soft tissue envelope that can be relied on to provide stability when reattached after implantation. The use of autograft or allograft ligament reconstruction members provides a means of accommodating varus/valgus movement by transferring forces to the medial and lateral ligaments of the elbow similar to what is experienced in vivo.

The prosthetic joint described above further provides for simplified surgery. The surgeon need not decide between hemi arthroplasty and total arthroplasty prior to performing the surgery, and can instead make this intraoperative decision. An easily replaced bearing is designed to wear in preference to components that are more difficult to replace. When the bearing wears out, which is anticipated to be a period of years, a relatively simple surgery may be used to replace the bearing.

A variety of modifications to the above-described embodiments will be apparent to those skilled in the art from this disclosure. For example, other methods of attaching ligament reconstruction methods between the respective joint components could be utilized without departing from the scope of the invention. Additionally, other hinge joints, such as knees, fingers, etc., may be repaired using a prosthetic joint described herein. Additionally, a ball and socket joint such as a shoulder or hip would equally benefit from the cementless attachment methods taught herein, as well as variations of ligament reconstruction utilizing tendons from the patient to secure the mating joint components. Thus, the invention may be embodied in other specific forms without departing from the spirit or essential attributes thereof. The particular embodiments disclosed are meant to be illustrative only and not limiting as to the scope of the invention. The appended claims, rather than to the foregoing specification, should be referenced to indicate the scope of the invention.

What is claimed is:

1. A prosthetic hinge elbow joint, the prosthetic hinge elbow joint defining an axis of rotation, the prosthetic hinge elbow joint comprising: a humeral component that is structured for attachment to a first bone, the humeral component defining a hole therein, the hole having a pair of open ends, one of the open ends being disposed on one side of the axis of rotation, the other of the open ends being disposed on the other side of the axis of rotation, the hole being dimensioned and configured to receive an autograft or allograft ligament reconstruction member passing completely therethrough when the prosthetic elbow joint is assembled within a patient; the humeral component including a spool, the hole for receiving the ligament reconstruction member being defined at least partially within the spool; and an ulnar component that is structured for attachment to a second bone, the ulnar component including a ligament retention member, the ligament retention member being secured to the ulnar component in a manner that permits compressing a portion of an autograft or allograft ligament reconstruction member between the ligament retention member and the second bone; whereby the autograft or allograft ligament reconstruction member is retained therein and permitted to incorporate with an exterior surface of the second bone.

2. The prosthetic hinge elbow joint according to claim 1, wherein the ulnar component includes at least one threaded fastener passing through a hole defined within the ligament retention member and threadedly engaging an internally threaded fastener receiver, whereby tightening the threaded fastener moves the ligament retention member closer to the second bone.

3. The prosthetic hinge elbow joint according to claim 1, wherein one of the humeral component and ulnar component includes at least one cross locking assembly, the at least one cross locking assembly being structured to resist rotation of either the humeral component or ulnar component with respect to a bone when the humeral component or ulnar component is installed within the bone, the cross locking assembly being structured to secure the ligament retention member to the ulnar component.

4. The prosthetic hinge elbow joint according to claim 3, wherein the cross locking assembly includes a threaded fastener, the threaded fastener passing through a hole defined within the ligament retention member and threadedly engaging an internally threaded fastener receiver, whereby tightening the threaded fastener moves the ligament retention member closer to the second bone.

5. The prosthetic hinge elbow joint according to claim 1, wherein: the humeral component includes a first intramedullary stem and a first connection portion, the first intramedullary stem being secured to the first connection portion; and the ulnar component includes a second intramedullary stem and a second connection portion, the second intramedullary stem being removably secured to the second connection portion.

* * * * *